US008815936B2

(12) United States Patent
Grant et al.

(10) Patent No.: US 8,815,936 B2
(45) Date of Patent: Aug. 26, 2014

(54) PHARMACEUTICAL FORMULATIONS OF RESVERATROL AND METHODS OF USE THEREOF FOR TREATING CELL DISORDERS

(75) Inventors: Ross Stewart Grant, Kellyville (AU); Nady Braidy, Riverwood (AU); Gilles Guillemin, Mount Colah (AU); George Smythe, Leichhardt (AU)

(73) Assignee: Nad Life Pty Ltd, Thornleigh, New South Wales (AU)

( * ) Notice: Subject to any disclaimer, the term of this patent is extended or adjusted under 35 U.S.C. 154(b) by 493 days.

(21) Appl. No.: 12/735,931

(22) PCT Filed: Mar. 3, 2009

(86) PCT No.: PCT/AU2009/000255
§ 371 (c)(1),
(2), (4) Date: Nov. 29, 2010

(87) PCT Pub. No.: WO2009/108999
PCT Pub. Date: Sep. 11, 2009

(65) Prior Publication Data
US 2011/0110913 A1 May 12, 2011

(30) Foreign Application Priority Data
Mar. 3, 2008 (AU) ................................ 2008901036

(51) Int. Cl.
*A01N 43/38* (2006.01)
*A01N 43/16* (2006.01)
*A01N 43/08* (2006.01)
*A01N 37/00* (2006.01)
*A01N 31/04* (2006.01)
*C07C 39/12* (2006.01)

(52) U.S. Cl.
USPC ........... 514/435; 514/458; 514/474; 514/578; 514/725; 568/729

(58) Field of Classification Search
USPC ........... 514/435, 458, 474, 578, 725; 568/729
See application file for complete search history.

(56) References Cited

U.S. PATENT DOCUMENTS

| 6,008,260 A | 12/1999 | Pezzuto et al. |
| 6,270,780 B1 | 8/2001 | Carson et al. |
| 6,414,037 B1 | 7/2002 | Pezzuto et al. |
| 6,790,869 B2 | 9/2004 | Ghai et al. |
| 6,878,751 B1 | 4/2005 | Donnelly et al. |
| 7,026,518 B2 | 4/2006 | Gokaraju et al. |
| 2001/0033848 A1 | 10/2001 | Jacobson et al. |
| 2002/0028852 A1 | 3/2002 | Ghai et al. |
| 2002/0173472 A1 | 11/2002 | Pezzuto et al. |
| 2006/0002914 A1 | 1/2006 | Milbrandt et al. |
| 2006/0269616 A1 | 11/2006 | Giampapa |
| 2006/0270732 A1 | 11/2006 | Giampapa |
| 2006/0276393 A1 | 12/2006 | Milburn et al. |
| 2006/0292099 A1 | 12/2006 | Milburn et al. |
| 2008/0015218 A1 | 1/2008 | Vazquez-Anon et al. |
| 2009/0169585 A1* | 7/2009 | Sardi ............................. 424/400 |

FOREIGN PATENT DOCUMENTS

| JP | 2001514661 A | 9/2001 |
| WO | 9903816 A1 | 1/1999 |
| WO | 0012534 A2 | 3/2000 |
| WO | WO 01/30336 | 5/2001 |
| WO | 03072187 A2 | 9/2003 |
| WO | 2004000302 A1 | 12/2003 |
| WO | 2004016726 A2 | 2/2004 |
| WO | 2006008470 A2 | 1/2006 |
| WO | WO 2006/001982 | 1/2006 |
| WO | 2006072809 A2 | 7/2006 |
| WO | WO 2006/128009 | 11/2006 |
| WO | 2008091710 A2 | 7/2008 |
| WO | 2009108999 A1 | 9/2009 |

OTHER PUBLICATIONS

Yu et al. Constitutive Accumulation of CIS-Piceid in Transgenic Arabidopsis Overexpressing a Sorghum Stilbene Gene; Plant Cell Physiology, vol. 47, No. 7 (2006) pp. 1017-1021.*
Svoboda et al. Natural Phenolics in the Prevention of UV-Induced Skin Damage. A Review; Biomedical Papers, vol. 147, No. 2 (2003) pp. 137-145.*
Slominski et al. On the Role of Melatonin in Skin Physiology and Pathology; Endocrine, vol. 27, No. 2 (2005) pp. 137-148.*
Otto et al. Differential Behaviors Toward Ultraviolet A and B Radiation in Fibroblasts and Keratinocytes From Normal and DNA-Repair-Deficient Patients; Cancer Research, vol. 59 (1999) pp. 1212-1218.*
Marambaued et al. Resveratrol Promotes Clearance of Alzheimer'S Disease Amyloid-Beta Peptides; The Journal of Biological Chemistry, vol. 280, No. 45 (2005) pp. 37377-37382.*
European Search Report for Application No. 09716592.2 dated Jan. 4, 2013.
Athar et al., Resveratrol: A Review of Preclinical Studies for Human Cancer Prevention, Toxicology and Applied Pharmacology, 2007, pp. 274-283, vol. 224, ScienceDirect.
Ara et al., Protective Effect of Resveratrol Against Oxidative Stress in Cholestasis, Journal of Surgical Research, 2005, pp. 112-117, vol. 127.
Anekonda, Thimmappa S., Resveratrol, A Boon for Treating Alzheimer's Disease? Brain Research Reviews, 2006, pp. 316-326, ScienceDirect.

(Continued)

*Primary Examiner* — Susan Hanley
*Assistant Examiner* — Paul Martin
(74) *Attorney, Agent, or Firm* — TraskBritt, P.C.

(57) ABSTRACT

Described is a composition for preventing or treating an oxidative stress related disease or condition in a subject. The disease or condition is characterized by the presence of excess oxidative compounds in the subject, and the composition includes a synergistic combination of therapeutically effective amounts of resveratrol to promote $NAD^+$ synthesis in the subject; a chelating agent to reduce production of additional oxidative compounds in the subject; and an antioxidant to minimize the oxidative activity in the subject.

12 Claims, 21 Drawing Sheets

(56) References Cited

OTHER PUBLICATIONS

Quincozes-Santos et al., Resveratrol Attenuates Oxidative-Induced DNA damage in C6 Glioma Cells, NeuroToxicology, 2007, pp. 886-891, vol. 28, ScienceDirect.

Burkhardt et al., DNA Oxidatively Damaged by Chromium (III) and $H_2O_2$ is Protected by the Antioxidants Melatonin, $N^1$-acetyl-$N^2$-formyl-5-methoxylcynuramine, Resveratrol and Uric Acid, The International Journal of Biochemistry & Cell Biology, 2001, pp. 775-783, vol. 33, Elsevier.

Database Medline [Online] US National Library of Medicine (NLM), Bethesda, MD, US, 2003, Morin et al., Evidence for Resveratrol-Induced Preservation of Brain Mitochondria Functions After Hypoxia-Reoxygenation, XP002688764, Database accession No. NLMI5134379 (Abstract).

Lagouge et al., Resveratrol Improves Mitochondrial Function and Protects Against Metabolic Disease by Activating SIRT1 and PGC-1α, Cell, 2006, pp. 1109-1122, vol. 127, Elsevier.

Belenky et al., NAD+ Metabolism in health and disease, Trends in Biochemical Sciences, 2006, pp. 12-19, vol. 32, No. 1, ScienceDirect.

PCT International Search Report, PCT/AU2009/000255, dated May 25, 2009.

Della-Morte et al., Resveratrol pretreatment protects rat brain from cerebral ischemic damage via a sirtuin I-uncoupling protein 2 pathway, Neuroscience, Mar. 31, 2009, pp. 993-1002, vol. 159, No. 3.

Raval et al., Resveratrol and ischemic preconditioning in the brain, Abstract, Curr. Med. Chem., 2008, pp. 1545-1551, vol. 15, No. 15, abstract only.

Howitz et al., (2003). "Small molecule activators of sirtuins extend *Saccharomyces cerevisiae* lifespan" Nature 425 (6954): pp. 191-196.

Wood et al., (2004). "Sirtuin activators mimic caloric restriction and delay aging in metazoans" Nature 430 (7000): pp. 686-689.

Jang et al., (1997). "Cancer chemopreventive activity of resveratrol, a natural product derived from grapes" Science 275 (5297): pp. 218-220.

Sun et al., (Jun. 1, 2002). "Induced overexpression of mitochondrial Mn-superoxide dismutase extends the life span of adult Drosophila melanogaster". Genetics 161 (2): pp. 661-172.

Hu et al., (Mar. 2007). "Hippocampal long-term potentiation, memory, and longevity in mice that overexpress mitochondrial superoxide dismutase". Neurobiol Learn Mem 87 (3): pp. 372-384.

Wong GH (May 1995). "Protective roles of cytokines against radiation: induction of mitochondrial MnSOD". Biochim. Biophys. Acta 1271 (1): pp. 205-209.

Berofsky et al., "An Improved Cycling Assay for Nicotinamide Adenine Dinucleotide" Anal Biochem (1973) 53: 452-458.

Bradford, Marion M., "A Rapid and Sensitive Method for the Quantitation of Microgram Quantities of Protein Utilizing the Principle of Protein-Dye Binding" Anal. Biochem (1976) 53: 452-458.

Cheung et al., "A Scintillation Proximity Assay for Poly(ADP-ribose) Polymerase" Anal Biochem (2000) 282: 24-28.

Farina et al.; "An Improved Synthesis of Resveratrol" Nat. Prod. Res. (2006) 20: 247-52.

Goldberg et al.; "Direct Injection Gas Chromatographic Mass Spectrometric Assay for trans-Resveratrol" Anal. Chem. (1994) 66: 3959-63.

Grant et al., "Murine Glial Cells Regenerate NAD, After Peroxide-Induced Depletion, Using Either Nicotinic Acid, Nicotinamide, or Quinolinic Acid as Substrates" J. Neurochem. (1998) 70(4): 1759-1763.

Jeandet et al, "The Production of Resveratrol (3,5,4'-trihydroxystilbene) by Grape Berries in Different Developmental Stages" Am. J. Enol. Vitic. (1991) 42: 41-46.

Klaidman et al., "High-Performance Liquid Chromatography Analysis of Oxidized and Reduced Pyridine Dinucleotides in Specific Brain Regions" Anal Biochem (1995) 225: 312-317.

Kumar, "Nano and Microparticles as Controlled Drug Delivery Devices" J Pharm Pharmaceut Sci (2000) 3 (2): 234-258.

Lamuela-Raventos, "Direct HPLC Analysis of cis- and trans-Resveratrol and Piceid Isomers in Spanish Red Vitis vinifera Wines" Agric. Food Chem (1995)(43): 281-283.

Nisselbaum et al., "A Simple Ultramicro Method for Determination of pyridine Nucleotides in Tissues" Anal Biochem (1969) 27: 212-217.

Putt et al., "An enzymatic assay for poly(ADP-ribose) polymerase-1 (PARP-1) via the chemical quantitation of NAD+: application to the high-throughput screening of small molecules as potential inhibitors" Anal Biochem (2004) 326:78-86.

Putt et al., "Direct Quantitation of Poly(ADP-Ribose) Polymerase (PARP) Activity as a Means to Distinguish Necrotic and Apoptotic Death in Cell and Tissue Samples" Chem. Bio. Chem (2005) 6: 53-55.

Sirtuin 1 obtained from http://en.wikipedia.org/wiki/Sirtuin_1Sirtuin 1 retrieved Dec. 17, 2013.

Wang et al., "An LC-MS Method for Analyzing Total Resveratrol in Grape Juice, Cranberry Juice and in Wine" J Agric Food Chem (2002) 50: 431-435.

International Preliminary Report on Patentability for PCT/AU2009/000255 dated Jun. 6, 2010.

Chapter II Demand for PCT/AU2009/000255 dated Nov. 16, 2009.

Response to Written Opinion for PCT/AU2009/000255 dated Feb. 2, 2010.

Baxter et al., Anti-aging properties of resveratrol: Review and report of a potent new antioxidant skin care formulation, Journal of Cosmetic Dermatology, vol. 7 No. 1, Mar. 1, 2008, pp. 207, abstract only.

* cited by examiner

| Treatment | Km | Vmax (nM/min.) |
|---|---|---|
| No Resveratrol | 115 | 83 |
| Resveratrol 50 μm | 83 | 130 |
| Resveratrol 100 μm | 62 | 430 |
| Resveratrol 200 μm | 43 | 506 |

PHARMACEUTICAL FORMULATIONS OF RESVERATROL AND METHODS OF USE THEREOF FOR TREATING CELL DISORDERS

TECHNICAL FIELD

The invention relates to methods and compositions for inducing DNA repair and $NAD^+$ synthesis in a subject. The invention further relates to methods and pharmaceutical compositions for the prevention and treatment of conditions and diseases associated with oxidative stress and/or DNA damage.

BACKGROUND ART

Nicotinamide adenine dinucleotide ($NAD^+$) is the parent compound of the pyridine nucleotide family of coenzymes (NADH, NADP, NADPH) that act as essential cofactors and electron transporters in a number of metabolic processes including alcohol, lactate and amino acid metabolism and energy (ATP) production. $NAD^+$ is an essential substrate for a number of important NAD-dependent enzymes including Poly(ADP-ribose) polymerase (PARP), Sir2-homolog (SIRT1) and NAD glycohydrolase ($CD38^+$). PARP is a nuclear enzyme which mediates repair of DNA double or single strand breaks, while the NAD-dependent deacetylase SIRT1 affects gene silencing and cellular longevity. NAD glycohydrolase catalyzes the production of cyclic ADP-ribose (cADPR) from $NAD^+$ and affects intracellular calcium signalling. The role of $NAD^+$ in these and other cellular functions suggest that in addition to being a regulator of metabolic activity, $NAD^+$ plays a central role in the control of fundamental cellular processes.

Maintenance of $NAD^+$ levels within both the cytoplasm and nucleus is therefore vital to sustaining nuclear integrity, cell viability and growth. Reduced levels of cellular $NAD^+$ consistently correlate with death in a number of cell types, and are prevalent in degenerative disorders associated with oxidative stress. Oxidative stress is characterised by the presence of excess oxidative compounds that may induce oxidative stress and/or damage, for example, reactive oxygen species (ROS), superoxide radical, hydroxyl radical, nitric oxide, ozone, thiyl radicals, and carbon-centred radicals (e.g., trichloromethyl radical). ROS such as $H_2O_2$, $O_2.-$, .OH and NO, have detrimental effects including inactivation of specific enzymes via oxidation of their co-factors, oxidation of polydesaturated fatty acids in lipids, oxidation of amino acids within proteins and DNA damage. Oxygen free radical activity is responsible for several important molecular cascades that underlie a number of pathologic processes including neurodegeneration, ischemia-reperfusion injury, atherosclerosis, inflammation, DNA damage in skin cells (e.g. keratinocytes and fibroblasts) and potentially tumor generation through deregulated cell signaling following DNA damage.

Increased ROS production is known to result from exposure to U.V. or ionising radiation (x-ray, γ-rays), chemical agents, infection, inflammation or reduced mitochondrial efficiency. Any one or combination of these factors may be prevalent in chronic degenerative states such as normal cellular aging, accelerated aging of the skin, Alzheimer's disease and Parkinson's disease, as well as chronic or acute UV induced damage in skin cells. Alzheimer's and Parkinson's diseases are examples of neurodegenerative disorders characterised by progressive loss of neuronal cells. The primary cause of brain cell death is not known but appears to be mediated by inflammatory changes associated with oxidative stress and accelerated DNA damage.

DNA strand breaks caused by oxidative damage require a rapid repair response which uses up the cells vital $NAD^+$ resource. While $NAD^+$ serves as a substrate for a number of enzymes, the most significant contributor to rapid $NAD^+$ turnover and depletion is activation of Poly(ADP-ribose) polymerase (PARP) enzyme family members, in particular PARP-1. As mentioned previously, PARP-1 is a DNA binding enzyme activated by double or single stranded breaks to the DNA and is critical to the base excision repair (BER) process. Although many proteins are involved in repairing DNA damage the majority of DNA lesions are repaired by BER. Accordingly, $NAD^+$ plays a central role in DNA repair and intracellular levels are rapidly reduced during oxidative stress. Improving antioxidant capacity and DNA repair is therefore a mechanism by which cell viability may be promoted and retained.

It is clear that maintaining $NAD^+$ levels within both the cytoplasm and nucleus is vital to sustaining nuclear integrity, cell viability and growth. Accordingly, there is a general need for treatments capable of increasing cellular levels of $NAD^+$ in circumstances where $NAD^+$ is depleted. Therapies for the treatment of oxidative stress have largely focused on the prevention of free radical production (chelation therapy) or the reduction of molecular damage (antioxidant therapy). Such treatments do not provide a means of alleviating DNA damage caused by ROS, and thus have limited potential in reducing cell death and deregulated cell growth (i.e. tumour proliferation). Hence, there is a need for treatments capable of enhancing DNA repair in diseases and conditions associated with chronic or acute oxidative stress.

DISCLOSURE OF INVENTION

In one aspect, the invention provides a method of inducing $NAD^+$ synthesis in a subject, said method comprising administering to the subject a therapeutically effective amount of resveratrol or a functionally equivalent analogue or derivative thereof. In one embodiment of the first aspect, the induction $NAD^+$ synthesis increases the activity of Poly(ADP-ribose) polymerase (PARP) enzymes. In one embodiment of the first aspect the PARP enzyme is PARP-1 or PARP-2.

In one embodiment of the first aspect, the induction of $NAD^+$ synthesis increases the activity of sirtuin enzymes. In one embodiment of the first aspect, the sirtuin enzyme is selected from the group consisting of SIRT1, SIRT2, SIRT3, SIRT4, SIRT5, SIRT6 and SIRT7.

In a second aspect, the invention provides a method of preventing or treating a disease or condition associated with oxidative stress, said method comprising administering to the subject a therapeutically effective amount of resveratrol or a functionally equivalent analogue or derivative thereof, wherein said administration induces $NAD^+$ synthesis in the subject.

In a third aspect, the invention provides a method of preventing or treating a disease or condition associated with DNA damage, said method comprising administering to the subject a therapeutically effective amount of resveratrol or a functionally equivalent analogue or derivative thereof.

In one embodiment of the second and third aspects, the disease or condition is a neurodegenerative disorder. In one embodiment of the second and third aspects, the neurodegenerative disorder is Alzheimer's disease or Parkinson's disease.

In one embodiment of the second and third aspects, the disease or condition is associated with accelerated aging of the skin.

In one embodiment of the second and third aspects, the disease or condition is UV induced DNA damage in skin cells and the skin cells may include keratinocytes and fibroblasts.

In one embodiment of the second and third aspect, the resveratrol or a functionally equivalent analogue or derivative thereof is administered as a triple therapy in a therapeutically effective amount.

In one embodiment of the second and third aspects the disease or condition associated with DNA damage is cancer.

In one embodiment of the second and third aspects, the disease or condition results from exposure to ultra-violet light, ionising radiation, exposure to chemical agents, infection, inflammation, reduced mitochondrial efficiency or combinations thereof.

In one embodiment of the first, second and third aspects, the resveratrol or functionally equivalent analogue or derivative is a trans-isomer.

In one embodiment of the first, second and third aspects method according to any one the functionally equivalent analogue of resveratrol is selected from the group consisting of hydroxylated resveratrol analogues, methoxylated resveratrol analogues, cis-resveratrol glucoside (cis-piceid) and trans-resveratrol-3-O-β-glucoside (trans-piceid).

In a fourth aspect, the invention provides a pharmaceutical composition when used for increasing $NAD^+$ synthesis comprising a therapeutically effective amount of resveratrol or a functionally equivalent analogue or derivative thereof.

In a fifth aspect, the invention provides pharmaceutical composition when used for the prevention or treatment of a disease or condition associated with oxidative stress comprising a therapeutically effective amount of resveratrol or a functionally equivalent analogue or derivative thereof, wherein said composition induces $NAD^+$ synthesis in the subject.

In a sixth aspect, the invention provides pharmaceutical composition when used for the prevention or treatment of a disease or condition associated with DNA damage comprising a therapeutically effective amount of resveratrol or a functionally equivalent analogue or derivative thereof, wherein said composition induces $NAD^+$ synthesis in the subject.

In one embodiment of the sixth aspect, the disease or condition is UV induced DNA damage in skin cells and the skin cells may include keratinocytes and fibroblasts.

In one embodiment of the sixth aspect, the resveratrol or a functionally equivalent analogue or derivative thereof is administered as a triple therapy in a therapeutically effective amount.

In a seventh aspect, the invention provides pharmaceutical composition when used for the prevention or treatment of a disease or condition associated with oxidative stress, said composition comprising a synergistic combination of at least one agent capable of inducing $NAD^+$ synthesis, and an effective amount of one or both of:
  (a) at least one antioxidant
  (b) at least one chelating agent In one embodiment of the seventh aspect, at least one agent capable of inducing $NAD^+$ synthesis is resveratrol or a functionally equivalent analogue or derivative thereof.

In one embodiment of the seventh aspect, the antioxidant is selected from the group consisting of melatonin, vitamin E, vitamin C, methionine, taurine, Superoxide dismutase (SOD), catalase (CAT), and glutathione peroxidase (GPX), L-ergothioneine N-Acetyl Cysteine (NAC), vitamin A, beta-carotene, retinol, catechins, epicatechins, epigallocatechin-3-gallate, flavenoids, L-ergothioneine, idebenone and selenium.

In one embodiment of the seventh aspect, the chelating agent is selected from the group consisting of ethylenediaminetetraacetic acid (EDTA), Ethylenediamine tetraacetic acid (calcium disodium versante) ($CaNa_2$-EDTA), Ethylene glycol tetraacetic acid (EGTA), dimercaptosuccinic acid (DMSA), Alpha lipoic acid (ALA), 2,3-dimercapto-1-propanesulfonic acid (DMPS), Dimercaprol (BAL), Deferoxamine, D-penicillamine, dimercaprol, Aminophenoxyethane-tetraacetic acid (BAPTA) Defarasirox, Diethylene triamine pentaacetic acid (DTPA), 2-pyridinecarboxylic acid (picolinic acid), 2,3-pyridinedicarboxylic acid (quinolinic acid), 2-aminobenzoic acid (anthranilic acid), kynurenic acid, xanthurenic acid and 8-hydroxyquinoline (and functional derivatives thereof).

In an eighth aspect, the invention provides a method for the treatment of a disease or condition associated with oxidative stress said method comprising administering to the subject a therapeutically effective amount of a pharmaceutical composition comprising a synergistic combination of at least one agent capable of inducing $NAD^+$ synthesis, and an effective amount of one or both of:
  (a) at least one antioxidant
  (b) at least one chelating agent In a ninth aspect, the invention provides a method for the treatment of a disease or condition associated with DNA damage said method comprising administering to the subject a therapeutically effective amount of a pharmaceutical composition comprising a synergistic combination of at least one agent capable of inducing $NAD^+$ synthesis, and an effective amount of one or both of:
  (a) at least one antioxidant
  (b) at least one chelating agent In one embodiment of the eighth aspect, the disease or condition is UV induced DNA damage in skin cells and the skin cells may include keratinocytes and fibroblasts.

In one embodiment of the eighth aspect, the resveratrol or a functionally equivalent analogue or derivative thereof is administered as a triple therapy in a therapeutically effective amount.

In one embodiment of the eighth and ninth aspects, the least one agent capable of inducing $NAD^+$ synthesis is resveratrol or a functionally equivalent analogue or derivative thereof.

In one embodiment of the eighth and ninth aspects, the antioxidant is selected from the group consisting of melatonin, vitamin E, vitamin C, methionine, taurine, Superoxide dismutase (SOD), catalase (CAT), and glutathione peroxidase (GPX), L-ergothioneine N-Acetyl Cysteine (NAC), vitamin A, beta-carotene, retinol, catechins, epicatechins, epigallocatechin-3-gallate, flavenoids, L-ergothioneine, idebenone and selenium.

In one embodiment of the eighth and ninth aspects, the chelating agent is selected from the group consisting of ethylenediaminetetraacetic acid (EDTA), Ethylenediamine tetraacetic acid (calcium disodium versante) ($CaNa_2$-EDTA), Ethylene glycol tetraacetic acid (EGTA), dimercaptosuccinic acid (DMSA), Alpha lipoic acid (ALA), 2,3-dimercapto-1-propanesulfonic acid (DMPS), Dimercaprol (BAL), Deferoxamine, D-penicillamine, dimercaprol, Aminophenoxyethane-tetraacetic acid (BAPTA) Defarasirox, Diethylene triamine pentaacetic acid (DTPA) 2-pyridinecarboxylic acid (picolinic acid), 2,3-pyridinedicarboxylic acid (quinolinic acid), 2-aminobenzoic acid (anthranilic acid), kynurenic acid, xanthurenic acid and 8-hydroxyquinoline (and functional derivatives thereof).

In a tenth aspect, the invention provides a kit for increasing $NAD^+$ synthesis in a subject comprising resveratrol or a functionally equivalent analogue or derivative thereof.

In an eleventh aspect, the invention provides a kit for treating a disease or condition associated with oxidative stress in a subject comprising resveratrol or a functionally equivalent analogue or derivative thereof.

In a twelfth aspect, the invention provides a kit for treating a disease or condition associated with DNA damage in a subject comprising resveratrol or a functionally equivalent analogue or derivative thereof.

In one embodiment of the twelfth aspect, the disease or condition is UV induced DNA damage in skin cells and the skin cells may include keratinocytes and fibroblasts.

In one embodiment of the twelfth aspect, the resveratrol or a functionally equivalent analogue or derivative thereof is administered as a triple therapy in a therapeutically effective amount.

In one embodiment of the tenth, eleventh and twelfth aspects, the resveratrol or functionally equivalent analogue or derivative is a trans-isomer.

In one embodiment of the tenth, eleventh and twelfth aspects, the functionally equivalent analogue is selected from the group consisting of hydroxylated resveratrol analogues, methoxylated resveratrol analogues, cis-resveratrol glucoside (cis-piceid) and trans-resveratrol-3-O-β-glucoside (trans-piceid).

Definitions

As used in this application, the singular form "a", "an" and "the" include plural references unless the context clearly dictates otherwise. For example, the term "a stem cell" also includes a plurality of stem cells.

As used herein, the term "comprising" means "including." Variations of the word "comprising", such as "comprise" and "comprises," have correspondingly varied meanings. Thus, for example, a polynucleotide "comprising" a sequence encoding a protein may consist exclusively of that sequence or may include one or more additional sequences.

As used herein, the term "resveratrol" encompasses either the cis-isomer of resveratrol, the trans-isomer of resveratrol, or a mixture of the two isomers. The term encompasses both the naturally occurring and chemically synthesized active agent and the compound as it may be in the laboratory. Further, when the term "resveratrol" is used herein, it is intended to encompass pharmacologically acceptable salts, esters, amides, prodrugs and derivatives and analogues of resveratrol.

As used herein, the term "synergistic" refers to a greater than additive effect that is produced by a combination of the agents, which exceeds the effect that would otherwise result from use of the agents alone.

A "therapeutically effective amount", as used herein, includes within its meaning a non-toxic but sufficient amount of the particular therapeutic compound to which it is referring to provide the desired therapeutic effect. The exact amount required will vary from subject to subject depending on factors such as the patient's general health, the patient's age and the stage and severity of the condition.

As used herein, the term "neurodegenerative disorder" refers to a disease or condition in an animal wherein there is a degeneration or inactivation of nerve cells in any location of the body including the brain, central nervous system and periphery.

As used herein, the term "oxidative stress" is used in general context and refers to enhanced generation of free radicals or reactive oxygen species (ROS) (such as α-hydroxy ethyl radical, hydrogen peroxide, peroxy radical, hydroxy radical, and superoxide radical) and/or a depletion in antioxidant defense system causing an imbalance between prooxidants and antioxidants. In general, oxidative stress involves the accumulation of free-radicals within the cell or the cell environment which may result in oxidative damage. Oxidative stress may arise from biotic (living) and abiotic (non-living) sources, for example, exposure to U.V. or ionising radiation or chemical agents, infection by different infectious agents, inflammation or reduced mitochondrial efficiency

BRIEF DESCRIPTION OF THE DRAWINGS

A preferred embodiment of the present invention will now be described, by way of an example only, with reference to the accompanying drawings wherein.

MODE(S) FOR CARRYING OUT THE INVENTION

Figure 1:
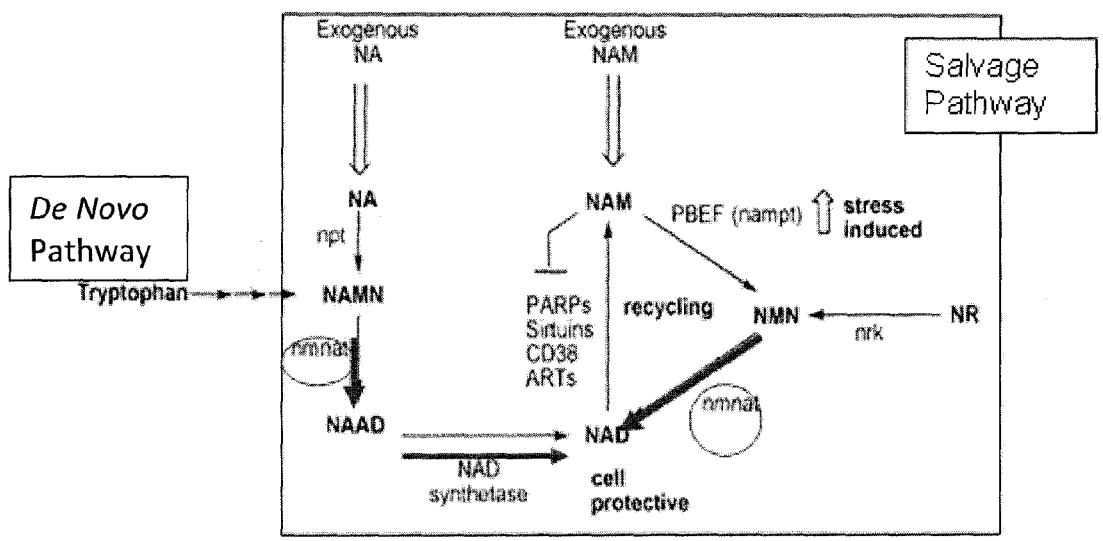
FIG. 1 is a diagram showing the synthesis of $NAD^+$ via the salvage pathway from nicotinamide (NAM) or Nicotinic acid (NA)

The invention relates to the finding that the intracellular synthesis of $NAD^+$ are increased by resveratrol (3,5,4'-trihydroxystilbene). While not being bound or limited to a particular mechanism, the inventors have demonstrated that resveratrol induces $NAD^+$ synthesis via the salvage pathway (shown in FIG. 1), specifically, by upregulation of nicotinamide mononucleotide adenylyl transferase (NMNAT) activity. Accordingly, the invention provides a means by which the intracellular synthesis of $NAD^+$ may be induced in a subject.

The inventors have also demonstrated that the induction of $NAD^+$ synthesis by administration of resveratrol provides a means of inducing DNA repair and promoting cellular viability and longevity. Again without being bound by a particular mechanism, it is believed that the upregulation of NMNAT activity by resveratrol has the effect of increasing the metabolism of nicotinamide (NAM), a precursor of $NAD^+$ and a by-product of Poly(ADP-ribose) polymerase (PARP) enzyme family members. NAM is an inhibitor of PARP enzymes (e.g. PARP-1) and mammalian sirtuin enzyme family members (SIRT1, SIRT2, SIRT3, SIRT4, SIRT5, SIRT6 and SIRT7). Metabolism of NAM induced by administration of resveratrol thus serves to increase available $NAD^+$ levels, while reducing inhibition of both PARP activity (thereby promoting DNA repair) and the activity of sirtuin enzymes (thereby promoting cell viability and longevity).

The invention further relates to the use of a promoter of $NAD^+$ synthesis, for example resveratrol, in combination with chelating agents and/or antioxidants to produce a synergistic effect for the treatment of conditions associated with oxidative stress. The inventors have demonstrated that the benefits derived from combination drug therapies consisting of an agent for chelating redox-active metals and an antioxidant to reduce damage caused by residual oxygen free radicals may be enhanced in a synergistic manner by the inclusion of a promoter of NAD$^+$ synthesis. It is believed that this synergistic effect arises from improved DNA repair (through at least increased PARP enzyme activity), and improved cell viability and longevity (through at least increased sirtuin activity), via increased production of their essential substrate NAD$^+$.

Resveratrol and NAD$^+$ Synthesis

Figure 2:
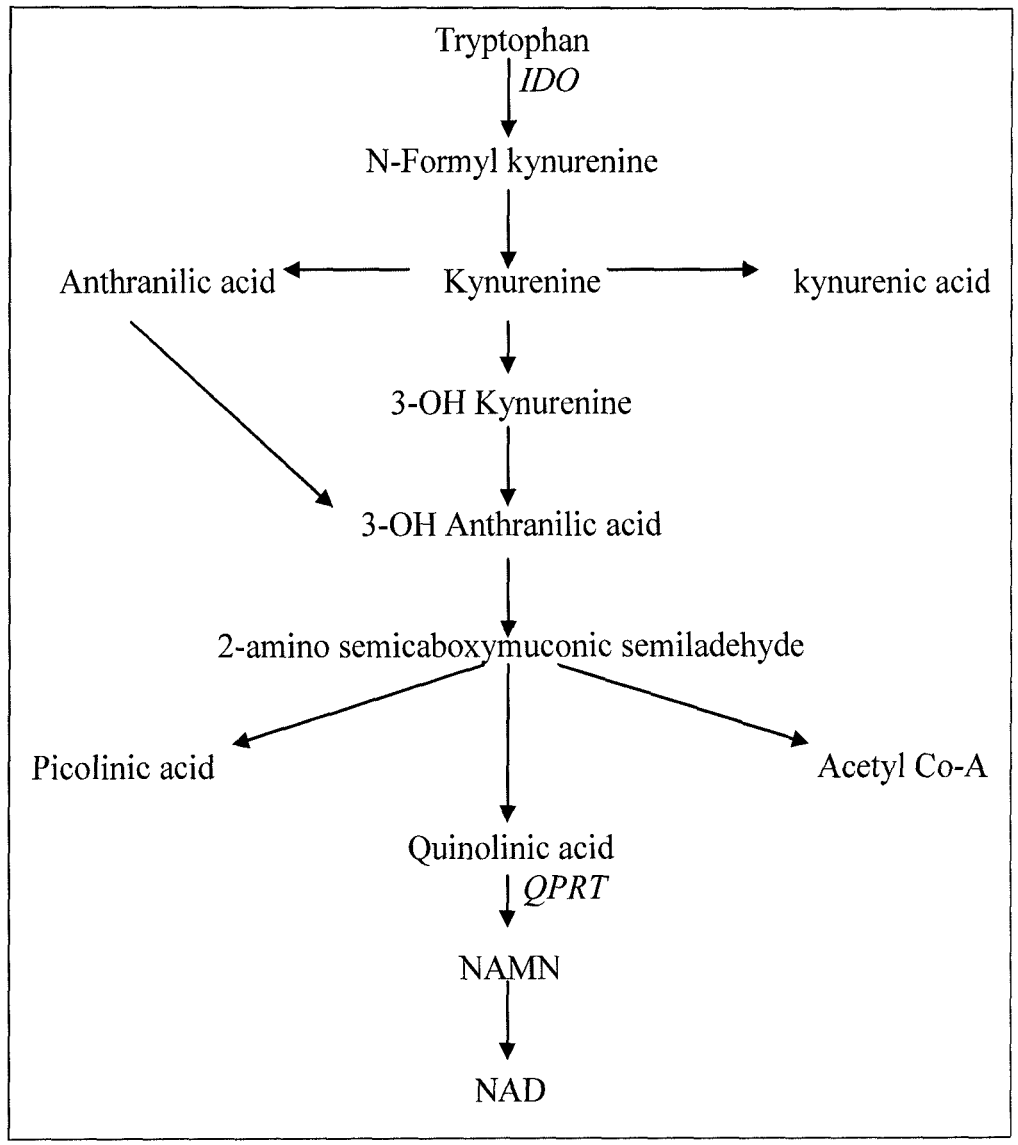
FIG. 2 is a diagram showing the synthesis of $NAD^+$ via the de novo pathway from tryptophan.

Nicotinamide adenine dinucleotide (NAD$^+$) can be synthesised from several different starting compounds. In the "de novo" pathway (shown in FIG. 2) NAD$^+$ is produced from the essential amino acid tryptophan. This pathway involves the generation of quinolinic acid from tryptophan, which is converted to nicotinic acid mononucleotide (NaMN) via the transfer of a phosphoribose group. An adenylate group is then transferred to form nicotinic acid adenine dinucleotide (NaAD). The nicotinic acid group of NaAD is then amidated to a nicotinamide group, forming NAD$^+$. Alternatively, nicotinamide or pre-formed compounds containing nicotinamide such as nicotinamide riboside are used to generate NAD$^+$ via the "salvage" pathway (see FIG. 1). Inhibition of enzymes in either the de novo or salvage pathway results in significant NAD$^+$ depletion highlighting the importance of both these pathways to the maintenance of cellular NAD$^+$ levels.

The invention provides a method of increasing the synthesis/level of intracellular NAD$^+$ in a subject. The method comprises administering to the subject a therapeutically effective amount of resveratrol or a functionally equivalent analogue or derivative thereof.

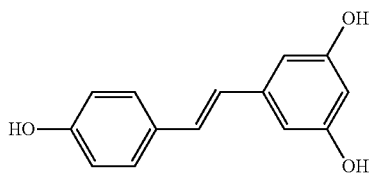 [SMILES: Oc1ccc(/C=C/c2cc(O)cc(O)c2)cc1]

Chemical Structure of Resveratrol
(3,5,4'-trihydroxystilbene)

In accordance with the methods of the invention, resveratrol (also known as 3,5,4'-trihydroxystilbene, trans-3,5,4'-trihydroxystilbene; 3,4',5-Stilbenetriol; trans-resveratrol; (E)-5-(p-Hydroxystyryl) resorcinol and resorcinol) may be administered in natural form, for example, as isolated from grape skins, wine or other plant-derived compositions using methods known in the art (see, for example, methods described in Lamuela-Raventos, *J. Agric. Food Chem.* (1995) (43): 281-283, and Wang et al. *J Agric Food Chem.* (2002) 50:431-435, the contents of which are incorporated herein by cross-reference). For example, ground plant material may be extracted using a suitable solvent such as methanol followed by concentration and dilution with water. After washing with an appropriate nonpolar organic solvent such as hexane the aqueous layer may be partitioned using, for example, ethyl acetate. The ethyl acetate extract may then be separated into fractions over a silica gel chromatographic column using, for example, chloroform-methanol as eluent. Fractions containing increased resveratrol concentration may be pooled together and subjected to further column chromatography.

Additionally or alternatively, resveratrol may be chemically synthesized, for example, using a Wittig reaction wherein two substituted phenols are linked through a styrene double bond, as described by Moreno-Manas et al. *Anal. Quim* (1985) 81:157-61, Jeand et al. *Am. J. Enol. Vitic.* (1991) 42:41-46, Goldberg et al. *Anal. Chem.* (1994) 66: 3959-63, and Farina et al. *Nat. Prod. Res.* (2006). 20: 247-52, the contents of which are incorporated herein by cross-reference. Additionally or alternatively, resveratrol for use in the invention may be obtained from commercial sources (e.g. from Sigma, St. Louis, Mo.).

Resveratrol for use in accordance with the invention may be in the form of a cis isomer, a trans isomer, or a mixture thereof. Cis-resveratrol may be derived from trans-resveratrol using methods known in the art, for example, by heating or exposing trans-resveratrol to ultraviolet irradiation followed by separation by HPLC and identification by mass spectrometry (MS). The invention also contemplates the use of functionally equivalent resveratrol derivatives and analogues. A resveratrol analogue is a compound that is based on resveratrol with substituted groups attached to the parent compound to produce a chemically-modified resveratrol compound. Examples of substituent groups include, but are not limited to $C_1$-$C_3$ alkyl (such as methyl, ethyl, propyl), $CH_2OH$, halogen (e.g., fluoro, chloro, bromo, iodo). Any one or more of the hydroxyl groups may be functionalised, e.g., with a protecting group. Suitable protecting groups are known to those skilled in the art and reference may be had to "Protective Groups in Organic Synthesis" by Theodora Greene and Peter Wuts (third edition, 1999, John Wiley and Sons). Alternatively, any one or more of the hydroxyl groups may be functionalised with, for example, $C_1$-$C_3$ alkyl (to form an ether), or a carboxylic acid group (to form an ester).

Examples of such compounds include hydroxylated or methoxylated resveratrol analogues. The functionally equivalent resveratrol analogue may be cis-resveratrol glucoside (cis-piceid) or trans-resveratrol-3-O-β-glucoside (trans-piceid). Derivatives of resveratrol include those in which one or more hydroxyl groups, typically the 3-hydroxyl group, is conjugated to a mono-saccharide or di-saccharide. In general, the 3-hydroxyl group may be conjugated to the 1-position of a monosaccharide. Examples of saccharides which may be conjugated to resveratrol include, but are not limited to, glucose, maltose, lactose, sucrose and galactose. Other derivatives and analogues of resveratrol suitable for use in the methods of the invention are described in, for example, U.S. Pat. No. 7,026,518, U.S. Pat. No. 6,790,869, PCT publication No. WO/2003/055444, PCT publication No. WO/2004/000302, PCT publication No. WO/1999/003816, the contents of which are incorporated herein by cross reference. The skilled addressee will recognise that the derivatives and analogues of resveratrol described herein are non-limiting examples and the invention encompasses the use of other such derivatives and analogues of resveratrol capable of inducing a functionally equivalent effect.

The invention also contemplates pharmaceutically acceptable salts of resveratrol and analogues thereof. S. M. Berge et al. describe pharmaceutically acceptable salts in detail in *J. Pharmaceutical Sciences*, 1977, 66:1-19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphorsulfonate, citrate, digluconate, cyclopentanepropionate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium potassium, calcium, magnesium, and the like, as well as non-toxic ammonium, quaternary ammonium, and amine cations, including, but not limited to ammonium, tetramethylammonium, tetraethylammonium, methylamine, dimethylamine, trimethylamine, triethylamine, ethylamine, triethanolamine and the like.

In accordance with the methods of the invention, the administration of therapeutically effective amounts of resveratrol to a subject may be used to induce the synthesis of intracellular $NAD^+$. Intracellular $NAD^+$ can be measured by methods known in the art and are described in, for example, Grant and Kapoor, *J. Neurochem*. (1998) 70(4): 1759-1763. Intracellular levels of $NAD^+$ can be measured, for example, using a high-performance liquid chromatography (HPLC) technique such as described by Klaidman et al., *Anal Biochem* (1995) 228:312-317, the contents of which are incorporated herein by reference. Additionally or alternatively, a spectrophotometric, microcycling assay may be used to measure intracellular levels of $NAD^+$, such as that described by Nisselbaum and Green, *Anal Biochem* (1969) 27: 212-217 or Berofsky and Swan, *Anal Biochem* (1973) 53: 452-458, the contents of which are incorporated herein by reference. For example, tissue/cell homogenate may be incubated in a pH controlled (buffered) solution, (reaction mixture), containing essential ingredients to facilitate the reaction of $NAD^+$ to a measurable compound. This reaction mixture may contain, for example ethanol, alcohol dehydrogenase, phenazine methosulfate and 3-[4,5-Dimethylthiazol-2-yl]-2,5-diphenyltetrazolium bromide, (MTT) (in bicine buffered solution). After a suitable incubation time, the reaction is then stopped with a suitable stopping reagent, for example, iodoacetic acid, and the level of $NAD^+$ in the sample determined by measurement against a reagent blank in a microplate reader.

$NAD^+$-dependent enzymes play an important role in DNA repair, particularly under conditions of oxidative stress. Accordingly, the invention provides a method of inducing DNA repair in a subject, the method comprising administering to the subject a therapeutically effective amount of resveratrol or a functionally equivalent analogue or derivative thereof. The induction of DNA repair in a subject may arise from the increased activity of one or more Poly(ADP-ribose) polymerase (PARP) enzyme family members. The activity of PARP enzymes can be measured using methods known in the art. For example PARP enzyme activity may be assayed by scintillation proximity assay (SPA) using biotinylated NAD as described by Cheung and Zhang *Anal Biochem* (2000) 282: 24-28, the contents of which are incorporated herein by reference. Additionally or alternatively, the activity of PARP enzymes may be measured using an enzymatic assay via the chemical quantitation of NAD as described by Karson et al., *Anal Biochem* (2004) 326: 78-86 or Putt et al., *Chem. Bio. Chem*. (2005) 6:53-55, the contents of which are also incorporated herein by reference. For example, plated cells or tissue are washed and then lysed using a suitable buffer solution containing excess $NAD^+$. A suitable buffer solution may comprise, for example, $MgCl_2$ (10 mM), Triton X-100 (1%), and $NAD^+$ (20 µM) in Tris buffer (50 mM, pH 8.1). As $NAD^+$ is the exclusive substrate for the PARP enzyme and is degraded during this reaction, total enzyme activity is determined by the reduction in $NAD^+$ concentration in the buffer solution over time. Following incubation for a suitable time period, the amount of $NAD^+$ consumed is measured by the NAD(H) microcycling assay as described above.

PARP enzymes consume $NAD^+$ as an adenosine diphosphate ribose (ADPR) donor and synthesize poly(ADP-ribose) onto nuclear proteins such as histones and PARP itself. Overactivation of PARP, particularly during oxidative stress, can cause significant depletion of cellular $NAD^+$ leading to cellular necrosis. Administration of resveratrol in accordance with the methods of the invention overcomes this problem firstly by increasing $NAD^+$ synthesis thus providing increasing the availability of substrate for PARP-mediated DNA repair, and secondly through the increased metabolism of nicotinamide (NAM) has the effect of removing an active inhibitor of PARP activity. PARP-1 is activated by DNA strand breaks and has been implicated in multiple DNA repair pathways, including the base excision repair (BER), single-strand break (SSB) and double-strand break (DSB) pathways. Binding of PARP-1 to damaged DNA via a double zinc finger DNA-binding domain potently activates PARP-1 activity thus allowing PARP-1 to also function as a DNA damage sensor. PARP-2 is also stimulated by damaged DNA and been implicated in base excision repair (BER) pathway via interactions with PARP-1 and X-ray repair cross-complementing group 1 (XRCC-1).

Nicotinamide (NAM) also inhibits the activity of mammalian sirtuin family enzymes such as SIRT1 on the Internet at en.wikipedia.org/wiki/Sir2-note-1. Administration of resveratrol in accordance with the methods of the invention increases $NAD^+$ synthesis thus increasing the availability of substrate necessary for sirtuin activity, while also reducing inhibition of sirtuin activity by inducing the increased metabolism of NAM. Accordingly, the invention provides a method of inducing sirtuin activity by the administration of resveratrol.

Pharmaceutical Compositions and Routes of Administration

The invention provides pharmaceutical compositions comprising a therapeutically effective amount of resveratrol or a functionally equivalent analogue or derivative thereof. The pharmaceutical compositions of the invention may be used for increasing $NAD^+$ synthesis in a subject in need thereof. Additionally or alternatively, the pharmaceutical compositions of the invention may be used for the prevention or treatment of a disease or condition associated with oxidative stress and/or DNA damage.

Resveratrol in the pharmaceutical compositions of the invention may be in the form of a cis isomer, a trans isomer, or a mixture thereof. Examples of resveratrol analogues suitable for the pharmaceutical compositions of the invention include, but are not limited to hydroxylated or methoxylated resveratrol analogues. The functionally equivalent resveratrol analogue may be cis-resveratrol glucoside (cis-piceid) or trans-resveratrol-3-O-β-glucoside (trans-piceid). Derivatives of resveratrol suitable for the pharmaceutical compositions of the invention include those in which one or more hydroxyl groups, typically the 3-hydroxyl group, is conjugated to a mono-saccharide or di-saccharide. In general, the 3-hydroxyl group may be conjugated the 1-position of a monosaccharide. Examples of saccharides which may be conjugated to resveratrol include, but are not limited to, glucose, maltose, lactose, sucrose and galactose. Other suitable resveratrol derivatives and analogues are described in, for example, U.S. Pat. No. 7,026,518, U.S. Pat. No. 6,790,869, PCT publication No. WO/2003/055444, PCT publication No. WO/2004/000302, PCT publication No. WO/1999/003816, the contents of which are incorporated herein by cross-reference. The skilled addressee will recognise that the derivatives and analogues of resveratrol suitable for the pharmaceutical compositions of the invention are non-limiting examples and the invention encompasses the use of other such derivatives and analogues of resveratrol capable of inducing a functionally equivalent effect.

Combination drug therapies consisting of an agent for chelating redox-active metals and/or an antioxidant to reduce damage caused by residual oxygen free radicals can be enhanced in a synergistic manner by the inclusion of a promoter of NAD$^+$ synthesis. Accordingly, the invention provides pharmaceutical compositions for the treatment of conditions and diseases associated with oxidative stress comprising a synergistic combination of at least one agent to promote NAD$^+$ synthesis, at least one antioxidant and/or at least one chelating agent.

The inclusion of an agent to promote NAD$^+$ synthesis in compositions containing an antioxidant and/or a chelating agent provides a synergistic effect for the prevention, treatment or alleviation of oxidative stress. In a preferred embodiment, the agent to promote of NAD$^+$ synthesis is resveratrol or a functional analogue or equivalent thereof. Without being bound to a particular mechanism, the provision of increased NAD$^+$ during conditions of oxidative stress may be beneficial to the function of other NAD$^+$-dependent enzymes, for example, NAD glycohydrolase, providing further beneficial effects for cells under oxidative stress. Additionally or alternatively, NAD$^+$ synthesis-promoting agents may have the capacity to increase activity of the NAD$^+$ dependant deacetylases such as sirtuin family enzymes (e.g. SIRT1) and promote improved DNA repair by enhancing PARP enzyme activity through increased production of their essential substrate NAD$^+$. Additionally or alternatively, NAD$^+$ synthesis-promoting agents may also be capable of increasing NAM metabolism via induction of NMNAT activity, thereby removing an inhibitor of PARP/sirtuins and further inducing the activity of those enzymes.

Chelating agents suitable for the synergistic compositions of the invention include, but are not limited to, ethylenediaminetetraacetic acid (EDTA), Ethylenediamine tetraacetic acid (calcium disodium versante) (CaNa$_2$-EDTA), Ethylene glycol tetraacetic acid (EGTA), dimercaptosuccinic acid (DMSA), Alpha lipoic acid (ALA), 2,3-dimercapto-1-propanesulfonic acid (DMPS), Dimercaprol (BAL), Deferoxamine, D-penicillamine, dimercaprol, Aminophenoxyethanetetraacetic acid (BAPTA) Defarasirox, Diethylene triamine pentaacetic acid (DTPA) 2-pyridinecarboxylic acid (picolinic acid), 2,3-pyridinedicarboxylic acid (quinolinic acid), 2-aminobenzoic acid (anthranilic acid), kynurenic acid, xanthurenic acid and 8-hydroxyquinoline (and functional derivatives thereof). In general, the chelating agent will be capable of forming complexes with redox-active metals in which the metal ion is generally bound to two or more atoms of the chelating agent thereby reducing hydroxyl radical production. The bonds may be any combination of coordination or ionic bonds. Examples of redox-active metals that may be bound and complexed by chelating agents include, but are not limited to Fe$^{++}$, Cu$^+$, Cr$^{+++}$, Mn$^{++}$, Co$^{++}$, Ni$^{++}$ Ag$^+$.

Antioxidants suitable for the synergistic compositions of the invention include, for but are not limited to, melatonin, vitamin E, vitamin C, methionine, taurine, superoxide dismutase (SOD), catalase (CAT), and glutathione peroxidase (GPX) and L-ergothioneine N-Acetyl Cysteine (NAC), vitamin A, beta-carotene, retinol, catechins, epicatechins, epigallocatechin-3-gallate, flavenoids, L-ergothioneine, idebenone and selenium. Other suitable antioxidants are described in US Patent No. 2008015218, the contents of which are incorporated herein by cross-reference.

The pharmaceutical compositions of the present invention may be administered therapeutically. In a therapeutic application, the compositions may be administered prophylactically in conditions expected to increase oxidative stress and/or DNA damage or to a patient already suffering from a disease or condition associated with oxidative stress and/or DNA damage, or at least partially arrest the disease or condition associated with oxidative stress and its complications. Single or multiple administrations of the pharmaceutical compositions can be carried out with dose levels and pattern being selected by the treating physician.

The therapeutically effective dose level for any particular patient will depend upon a variety of factors including: the severity of the disease or condition associated with oxidative stress and/or DNA damage, including UV induced DNA damage in skin cells, the composition employed, the age, body weight, general health and diet of the patient, the time of administration, the route of administration, the duration of the treatment, drugs used in combination or coincidental with the synergistic composition, together with other related factors well known in medicine.

One skilled in the art would, by routine experimentation, be able to determine an effective, non-toxic amount of this treatment regime which would be required to treat a disease or condition associated with oxidative stress and/or DNA damage, including UV induced DNA damage in skin cells, with the pharmaceutical compositions of the present invention.

In the methods of the invention, the pharmaceutical compositions administered may be in the range of about 0.0001 mg to about 1000 mg per kg body weight; for example, about 0.001 mg to about 750 mg per kg body weight; about 0.01 mg to about 500 mg per kg body weight; about 0.1 mg to about 500 mg per kg body weight; about 0.1 mg to about 250 mg per kg body weight; or about 1.0 mg to about 250 mg per kg body weight. More suitably, an effective dosage per 24 hours may be in the range of about 1.0 mg to about 200 mg per kg body weight; about 1.0 mg to about 100 mg per kg body weight; about 1.0 mg to about 50 mg per kg body weight; about 1.0 mg to about 25 mg per kg body weight; about 5.0 mg to about 50 mg per kg body weight; about 5.0 mg to about 20 mg per kg body weight; or about 5.0 mg to about 15 mg per kg body weight.

Further, it will be apparent to one of ordinary skill in the art that the optimal quantity and spacing of individual dosages of the compositions of the present invention will be determined by the nature and extent of the condition the form, route and site of administration, and the nature of the particular patient being treated. Also, such optimum conditions can be determined by conventional techniques.

It will also be apparent to one of ordinary skill in the art that the optimal course of treatment, such as the number of doses of the composition of the present invention given per day for a defined number of days, can be ascertained by those skilled in the art using conventional course of treatment determination tests.

In general, pharmaceutical compositions of the present invention may be prepared according to methods which are known to those of ordinary skill in the art, and accordingly may include a pharmaceutically acceptable carrier, diluent and/or adjuvant.

According to the methods of present invention, the pharmaceutical compositions may be administered by any suitable route, either systemically, regionally or locally. The particular route of administration to be used in any given circumstance will depend on a number of factors, including the nature of the disease or condition to be treated, the severity and extent of the disease or condition, the required dosage of the particular compounds to be delivered and the potential side-effects of the compounds.

For example, in circumstances where it is required that appropriate concentrations of the desired compounds are delivered directly to the site in the body to be treated, administration may be regional rather than systemic. Regional administration provides the capability of delivering very high local concentrations of the desired compounds to the required site and thus is suitable for achieving the desired therapeutic or preventative effect whilst avoiding exposure of other organs of the body to the compounds and thereby potentially reducing side effects.

By way of example, administration according to embodiments of the invention may be achieved by any standard routes, including intracavitary, intravesical, intramuscular, intraarterial, intravenous, subcutaneous, topical or oral. Intracavitary administration may be intraperitoneal or intrapleural. In particular embodiments, administration may be via intravenous infusion or intraperitoneal administration.

If desired, devices or compositions containing the pharmaceutical compositions suitable for sustained or intermittent release could be, in effect, implanted in the body or topically applied thereto for the relatively slow release of such materials into the body.

The carriers, diluents and adjuvants must be "acceptable" in terms of being compatible with the other components of the composition, and not deleterious to the recipient thereof. Examples of pharmaceutically acceptable carriers or diluents are demineralised or distilled water, saline solution, vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones, mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose, lower alkanols, for example ethanol or iso-propanol; lower aralkanols, lower polyalkylene glycols or lower alkylene glycols, for example polyethylene glycol, polypropylene glycol, ethylene glycol, propylene glycol, 1,3-butylene glycol or glycerine, fatty acid esters such as isopropyl palmitate, isopropyl myristate or ethyl oleate, polyvinylpyrridone, agar, carrageenan; gum tragacanth or gum acacia, and petroleum jelly. The carrier or carriers may form from between 10% to 99.9% by weight of the compositions.

The pharmaceutical compositions of the invention may be in the form of a composition in a form suitable for administration by oral ingestion (such as capsules, tablets, caplets and elixirs, for example), in the form of an ointment, cream or lotion suitable for topical administration, which would be particularly preferred for the treatment and repair of UV induced DNA damage in skin cells, in a form suitable for delivery as an eye drop, in an aerosol form suitable for administration by inhalation, such as by intranasal inhalation or oral inhalation, in a form suitable for parenteral administration, that is subcutaneous, intramuscular or intravenous injection.

For administration as an injectable solution or suspension, non-toxic parenterally acceptable diluents or carriers can include Ringer's solution, isotonic saline, phosphate buffered saline, ethanol and 1,2-propylene glycol.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition, these oral formulations may contain suitable flavouring and colourings agents. When used in capsule form the capsules may be coated with compounds such as glyceryl monostearate or glyceryl distearate which delay disintegration.

Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

Pharmaceutical compositions of the invention may be prepared by blending, grinding, homogenising, suspending, dissolving, emulsifying, dispersing and/or mixing the selected therapeutic compound with the selected excipient(s), carrier(s), adjuvant(s) and/or diluent(s).

One type of pharmaceutical composition of the invention in the form of a tablet or capsule may be prepared by (a) preparing a first tablet or a capsule comprising a first therapeutic compound, together with any desired excipient(s), carrier(s), adjuvant(s) and/or diluent(s), and (b) preparing a second tablet or a capsule, wherein the second tablet or the capsule includes a second therapeutic compound and the first tablet or capsule.

Another type of pharmaceutical composition of the invention in the form of a capsule may be prepared by (a) preparing a first capsule comprising a first therapeutic compound together with any desired excipient(s), carrier(s), adjuvant(s) and/or diluent(s), and (b) preparing a second capsule, wherein the second capsule includes a second therapeutic compound and the first capsule.

A further type of pharmaceutical composition of the invention in the form of a tablet may be prepared by (a) preparing a capsule comprising an therapeutic compound together with any desired excipient(s), carrier(s), adjuvant(s) and/or diluent(s), and (b) preparing a tablet, wherein the tablet includes the second therapeutic compound and the capsule.

The emulsions for oral administration may further comprise one or more emulsifying agents. Suitable emulsifying agents include dispersing agents as exemplified above or natural gums such as guar gum, gum acacia or gum tragacanth.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by cross-reference.

The topical compositions of the invention, comprise an therapeutic compound(s) together with one or more acceptable carriers, and optionally any other therapeutic ingredients. Compositions suitable for topical administration include liquid or semi-liquid preparations suitable for penetration through the skin to the site of where treatment is required, such as liniments, lotions, creams, ointments or pastes, and drops suitable for administration to the eye, ear or nose.

Drops according to the present invention may comprise sterile aqueous or oily solutions or suspensions. These may be prepared by dissolving the therapeutic compound(s) in an aqueous solution of a bactericidal and/or fungicidal agent and/or any other suitable preservative, and optionally including a surface active agent. The resulting solution may then be clarified by filtration, transferred to a suitable container and sterilised. Sterilisation may be achieved by: autoclaving or maintaining at 90° C.-100° C. for half an hour, or by filtration, followed by transfer to a container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the invention include those suitable for application to the skin or eye. An eye lotion may comprise a sterile aqueous solution optionally containing a bactericide and may be prepared by methods similar to those described above in relation to the preparation of drops. Lotions or liniments for application to the skin may also include an agent to hasten drying and to cool the skin, such as an alcohol or acetone, and/or a moisturiser such as glycerol, or oil such as castor oil or arachis oil.

Creams, ointments or pastes according to the invention are semi-solid formulations of the compound(s) for external application. They may be made by mixing the active ingredient in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols.

The compositions may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

The compositions may also be administered or delivered to target cells in the form of liposomes. Liposomes are generally derived from phospholipids or other lipid substances, and are formed by mono- or multi-lamellar hydrated liquid crystals that are dispersed in an aqueous medium. Specific examples of liposomes used in administering or delivering a composition to target cells are synthetic cholesterol (Sigma), the phospholipid 1,2-distearoyl-sn-glycero-3-phosphocholine (DSPC; Avanti Polar Lipids), the PEG lipid 3-N-[(-methoxy poly(ethylene glycol)2000)carbamoyl]-1,2-dimyrestyloxypropylamine (PEG-cDMA), and the cationic lipid 1,2-di-o-octadecenyl-3-(N,N-dimethyl)aminopropane (DODMA) or 1,2-dilinoleyloxy-3-(N,N-dimethyl)aminopropane (DLinDMA) in the molar ratios 55:20:10:15 or 48:20:2:30, respectively, PEG-cDMA, DODMA and DLinDMA. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which is incorporated herein by cross-reference.

The compositions may also be administered in the form of microparticles. Biodegradable microparticles formed from polylactide (PLA), polylactide-co-glycolide (PLGA), and epsilon-caprolactone (ε-caprolactone) have been extensively used as drug carriers to increase plasma half life and thereby prolong efficacy (R. Kumar, M., 2000, *J Pharm Pharmaceut Sci.* 3(2) 234-258). Microparticles have been formulated for the delivery of a range of drug candidates including vaccines, antibiotics, and DNA. Moreover, these formulations have been developed for various delivery routes including parenteral subcutaneous injection, intravenous injection and inhalation.

The compositions may incorporate a controlled release matrix that is composed of sucrose acetate isobutyrate (SAIB) and organic solvent or organic solvents mixture. Polymer additives may be added to the vehicle as a release modifier to further increase the viscosity and slow down the release rate. SAIB is a well known food additive. It is a very hydrophobic, fully esterified sucrose derivative, at a nominal ratio of six isobutyrate to two acetate groups. As a mixed ester, SAIB does not crystallize but exists as a clear viscous liquid. Mixing SAIB with a pharmaceutically accepted organic solvent such as ethanol or benzyl alcohol decreases the viscosity of the mixture sufficiently to allow for injection. A therapeutic compound(s) may be added to the SAIB delivery vehicle to form SAIB solution or suspension formulations. When the formulation is injected subcutaneously, the solvent diffuses from the matrix allowing the SAIB-drug or SAIB-drug-polymer mixtures to set up as an in situ forming depot.

Those skilled in the art will appreciate that in accordance with the methods of the invention the pharmaceutical compositions may be administered alone or in conjunction with one or more additional agents as a combination therapy. For example, a pharmaceutical composition of the invention may be administered together with one or more additional agents capable of treating or preventing conditions associated with oxidative stress and/or DNA damage, including UV induced DNA damage in skin cells.

For such combination therapies, each component of the combination therapy may be administered at the same time, or sequentially in any order, or at different times, so as to provide the desired effect. Alternatively, the components may be formulated together in a single dosage unit as a combination product. When administered separately, it may be preferred for the components to be administered by the same route of administration, although it is not necessary for this to be so.

Therapeutic advantages may be realised through combination regimens. In combination therapy the respective compositions and any other agents may be administered simultaneously or sequentially in any order. Accordingly, methods of treatment according to the invention may be applied in conjunction with conventional therapy, such as radiotherapy, chemotherapy, surgery, or other forms of medical intervention. Examples of chemotherapeutic agents include adriamycin, taxol, fluorouricil, melphalan, cisplatin, oxaliplatin, alpha interferon, vincristine, vinblastine, angioinhibins, TNP-470, pentosan polysulfate, platelet factor 4, angiostatin, LM-609, SU-101, CM-101, Techgalan, thalidomide, SP-PG and the like. Other chemotherapeutic agents include alkylating agents such as nitrogen mustards including mechloethamine, melphan, chlorambucil, cyclophosphamide and ifosfamide, nitrosoureas including carmustine, lomustine, semustine and streptozocin; alkyl sulfonates including busulfan; triazines including dicarbazine; ethyenimines including thiotepa and hexamethylmelamine; folic acid analogues including methotrexate; pyrimidine analogues including 5-fluorouracil, cytosine arabinoside; purine analogues including 6-mercaptopurine and 6-thioguanine; antitumour antibiotics including actinomycin D; the anthracyclines including doxorubicin, bleomycin, mitomycin C and methramycin; hormones and hormone antagonists including tamoxifen and cortiosteroids and miscellaneous agents including cisplatin and brequinar, and regimens such as COMP (cyclophosphamide, vincristine, methotrexate and prednisone), etoposide, mBACOD (methotrexate, bleomycin, doxorubicin, cyclophosphamide, vincristine and dexamethasone), and PROMACE/MOPP (prednisone, methotrexate (w/leucovin rescue), doxorubicin, cyclophosphamide, taxol, etoposide/mechlorethamine, vincristine, prednisone and procarbazine).

Those skilled in the art will appreciate that the invention described herein is susceptible to variations and modifications other than those specifically described. It is to be understood that the invention includes all such variations and modifications.

Methods of Treatment

The invention contemplates methods for treating diseases and conditions associated with oxidative stress and/or DNA damage, including UV induced DNA damage in skin cells. In one embodiment, the method comprises the administration to a subject of a therapeutically effective amount of resveratrol or a functionally equivalent analogue or derivative thereof. In another embodiment, the method comprises administering to the subject a therapeutically effective amount of a pharmaceutical composition comprising a synergistic combination of at least one agent that induces NAD synthesis, and an effective amount of one or both of at least one antioxidant and at least one chelating agent.

The skilled addressee will recognise that administration of the compositions of the invention can be used to directly target the stimulation of $NAD^+$ synthesis thus providing beneficial effects for treatment of oxidative stress and/or DNA damage, including UV induced DNA damage in skin cells, involving increased levels of reactive oxygen species such as $H_2O_2$, $O_2.-$, .OH and NO. Increased synthesis of $NAD^+$ provides additional substrate for PARP enzymes involved in DNA repair and sirtuin enzymes, while also increasing nicotinamide metabolism thus removing a potent inhibitor of PARP and sirtuin enzyme activity. Accordingly, the methods of the invention provide a means of alleviating the critical reduction in $NAD^+$ levels and proportionate increased levels of cell death oxidative stress-induced PARP activation.

Diseases and conditions associated with oxidative stress and/or DNA damage, including UV induced DNA damage in skin cells suitable for treatment by the methods of the invention include, but are not limited to those in which increased levels of ROS result from exposure to U.V. or ionising radiation (e.g. x-ray, γ rays), chemical agents, infection, inflammation or reduced mitochondrial efficiency. The methods of the invention are suitable for the treatment of normal cellular ageing or accelerated ageing of the skin, treatment and repair of UV induced DNA damage in skin cells (i.e. keratinocytes and fibroblasts) and neurodegenerative diseases and disorders including, for example, Alzheimer's disease and Parkinson Disease. Additionally or alternatively, the methods of the invention suitable for the treatment of diseases and conditions associated with DNA damage including, for example, cancer. The skilled addressee will recognise that the diseases referred to above are non-limiting examples and the compositions of the invention may be used for the treatment of other conditions and diseases associated with oxidative stress and/or DNA damage.

Kits

The invention provides kits for increasing $NAD^+$ synthesis, the kit comprising resveratrol or a functionally equivalent analogue or derivative thereof.

Also provided are kits for treating a disease or condition associated with oxidative stress in a subject comprising resveratrol or a functionally equivalent analogue or derivative thereof.

Further provided are kits for treating a disease or condition associated with DNA damage, including UV induced DNA damage in skin cells in a subject comprising resveratrol or a functionally equivalent analogue or derivative thereof.

The resveratrol or functionally equivalent analogue or derivative may be a cis-isomer, a trans-isomer or a mixture thereof. Resveratrol analogues that may be included in the kit include, but are not limited to methoxylated resveratrol analogues, cis-resveratrol glucoside (cis-piceid) and trans-resveratrol-3-O-β-glucoside (trans-piceid).

The kit may comprise any number of additional components. By way of non-limiting examples the additional components may include reference samples, buffers, labels, and written instructions for performing the assay.

The invention will now be described with reference to specific examples, which should not be construed as in any way limiting the scope of the invention.

EXAMPLES

Example 1

Inhibition of the De Novo Pathway of $NAD^+$ Synthesis by the IDO Inhibitor 1-MT in Human Foetal Astrocytes Primary human foetal astrocytes were seeded into 24 well culture plates (~$10^5$ cells/well). Each well contained 1 ml of RPMI 1640 cell culture medium supplemented with 10% foetal bovine serum (FBS) and 0.5% Glutamax. Cultures were left to equilibrate for 24 hours before treatment with the IDO inhibitor 1-methyl tryptophan (1-MT) (100 μM) alone or in combination with either L-tryptophan (100 μM) or Nicotinic acid (100 μM). Following the addition of drug, cultures were incubated for 24 hours at 37° C. in 5% $CO_2$ before analysis of cellular $NAD^+$ concentration. Cells were washed with TRIS buffer (pH7.4) and sonicated in a homogenate solution containing nicotinamide (10 mM) as a PARP inhibitor. A sample of cell homogenate was then added to a reaction mixture containing bicine buffer (120 mM), ethanol (0.6M), Phenyzine methyl sulfate (PMS) (2 mM), MIT (0.5 mM) and alcohol dehydrogenase (1 mg/ml). $NAD^+$+NADH levels were quantified spectrophotometrically against a reagent blank using a 570 nm filter in a BioRad X680 microplate reader (BioRad, Hercules Calif.).

$NAD^+(H)$ concentrations per cell were adjusted for varying levels of protein by referencing against the total amount of protein in the cell homogenate.

Total protein was determined using the Bradford Protein assay. Briefly, 10 μl of sample cell homogenate (used in $NAD^+$ assay) was added into each well with 230 μl of MILLI-Q® water and 60 μl of Bradford reagent and left to equilibrate for 10-15 min. The plate was then read using a 595 nm filter in a BioRad X680 microplate reader (BioRad, Hercules Calif.).

Figure 3:
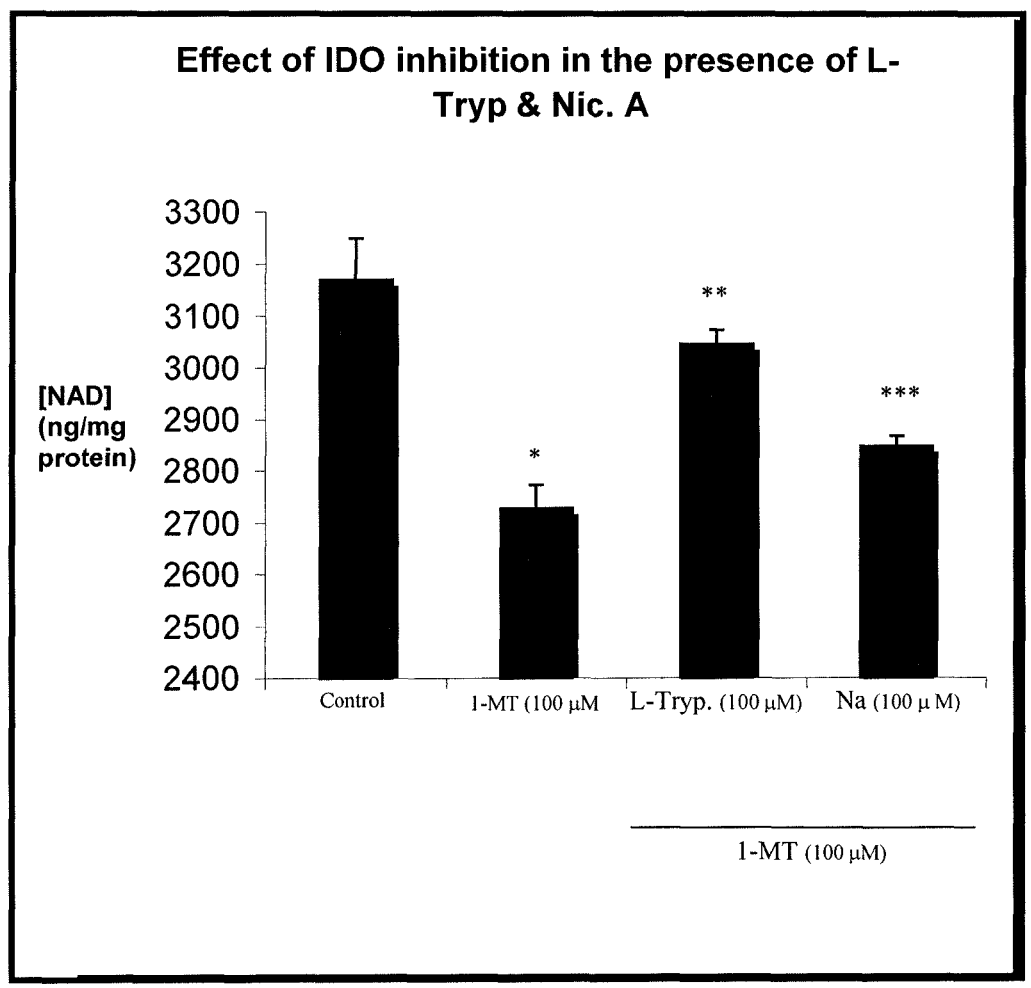
FIG. 3 is a graph showing the effect of the indoleamine 2,3-dioxygenase (IDO) inhibitor 1-MT on intracellular $NAD^+$ levels in cultured human foetal astrocytes. Human foetal astrocytes were treated with 1-MT alone, or combinations of 1-MT/L-tryptophan (1-Tryp) and 1-MT/nicotinic acid (Nic a). *$p<0.05$ compared to control, $p<0.05$ compared to 1-MT treatment alone, **$p<0.05$ compared to L-tryp+1-MT treated cells.

Complete inhibition of de novo synthesis of $NAD^+$ from tryptophan was induced by the competitive IDO inhibitor 1-MT (1 mM, 24 h) resulting in a significant decrease in intracellular $NAD^+$ levels (FIG. 3). Supplementation with either excess L-tryptophan or the salvage pathway substrate nicotinic acid partially reversed the $NAD^+$ depletion compared to 1-MT treatment alone (FIG. 3).

Example 2

$H_2O_2$ Increases PARP Activity in Human Foetal Astrocytes

Primary human foetal astrocytes were seeded into 24 well culture plates (~$10^5$ cells/well). Each well contained 1 ml of RPMI 1640 cell culture medium supplemented with 10% foetal bovine serum (FBS) and 0.5% Glutamix. Cultures were left to equilibrate for 24 hours before treatment with the pro-oxidant $H_2O_2$ at increasing concentration between 0 μM and 1000 μM. Following the addition of the $H_2O_2$ cultures were incubated for 15 minutes at 37° C. in 5% $CO_2$ before being washed twice and homogenised/lysed in 200 μL of PARP assay buffer containing $MgCl_2$ (10 mM), Triton X-100 (1%), and $NAD^+$ (20 μM) in Tris buffer (50 mM, pH 8.1) and left to incubate for 60 minutes at 37° C. As $NAD^+$ is the exclusive substrate for the PARP enzyme and is degraded during this reaction, total enzyme activity is determined by quantitating the reduction in $NAD^+$ concentration in the assay buffer solution. The amount of $NAD^+$ consumed is measured by the $NAD^+(H)$ microcycling assay as previously above.

Figure 4:
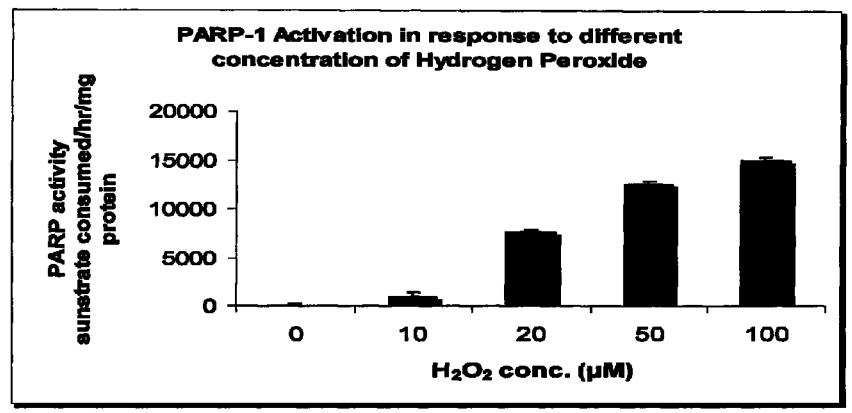
FIG. 4 is a graph showing the effect of different concentrations of hydrogen peroxide ($H_2O_2$) on PARP activity in cultured human foetal astrocytes. $^\alpha p<0.05$ compared to no $H_2O_2$; $^\beta p<0.05$ compared to 10 μM $H_2O_2$; $^\chi p<0.05$ compared to 20 μM $H_2O_2$; $^\delta p<0.05$ compared to 50 μM $H_2O_2$.

PARP-1 activity was significantly increased in cultured human foetal astrocytes following exposure to 10-100 μM $H_2O_2$ for 20 min (FIG. 4) ($^\alpha p<0.05$ compared to no $H_2O_2$; $^\beta p<0.05$ compared to 10 μM $H_2O_2$; $^\chi p<0.05$ compared to 20 μM $H_2O_2$; $^\delta p<0.05$ compared to 50 μM $H_2O_2$).

Example 3

$H_2O_2$ Decreases Intracellular $NAD^+$ in Human Foetal Astrocytes

Primary human foetal astrocytes were seeded into 24 well culture plates (~$10^5$ cells/well). Each well contained 1 ml of RPMI 1640 cell culture medium supplemented with 10% foetal bovine serum (FBS) and 0.5% Glutamix. Cultures were left to equilibrate for 24 hours before treatment with the prooxidant $H_2O_2$ at increasing concentration between 0 μM and 1000 μM. Following the addition of the $H_2O_2$ cultures were incubated for 15 minutes at 37° C. in 5% $CO_2$ before being washed twice and resuspended in 300 μL PBS and placed on ice before sonication and immediate analysis of cellular NAD levels as described in Example 1 above.

Figure 5:
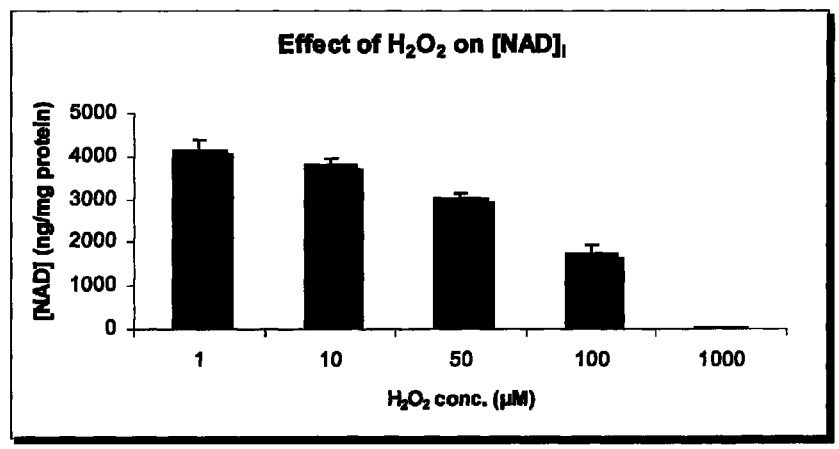
FIG. 5 is a graph showing the effect of different concentrations of hydrogen peroxide ($H_2O_2$) on intracellular $NAD^+$ in cultured human foetal astrocytes. *$p<0.05$ compared to 0 μM $H_2O_2$ control, $p<0.05$ compared to 50 μM $H_2O_2$, *$p<0.05$ compared to 100 μM $H_2O_2$.

Intracellular $NAD^+$ was significantly decreased in cultured human foetal astrocytes following exposure to 10-100 μM $H_2O_2$ for 20 min (FIG. 5) (*$p<0.05$ compared to 0 μM $H_2O_2$ control, $p<0.05$ compared to 50 μM $H_2O_2$, *$p<0.05$ compared to 100 μM $H_2O_2$). The reduction in $NAD^+$ levels was inversely correlated to measured PARP-1 activity (shown in FIG. 4).

Example 4

$H_2O_2$ Induces LDH Release in Human Foetal Astrocytes

Primary human foetal astrocytes were seeded into 24 well culture plates (~$10^5$ cells/well). Each well contained 1 ml of RPMI 1640 cell culture medium supplemented with 10% foetal bovine serum (FBS) and 0.5% Glutamix. Cultures were left to equilibrate for 24 hours before treatment with the pro-oxidant $H_2O_2$ at increasing concentration between 0 and 1000 μM. Following the addition of the $H_2O_2$ cultures were incubated for 20 minutes at 37° C. in 5% $CO_2$ before supernatants were withdrawn and analysed for LDH activity. As LDH is a cytoplasmic enzyme, leakage of LDH into the cell culture supernatant is widely used as a measure of overall cell viability. Briefly, 50 μl of pyruvate (11.5 mM) is added to 50 μl of cell culture supernatant. A further 100 μl of NADH solution (700 μM) is added to the wells. LDH activity is measured spectrophotometrically by monitoring the change in absorbance at 340 nm over 5 min., using a BioRad X680 microplate reader (BioRad, Hercules Calif.) and calculating the maximal rate of change in absorbance over the linear portion of the curve.

Figure 6:
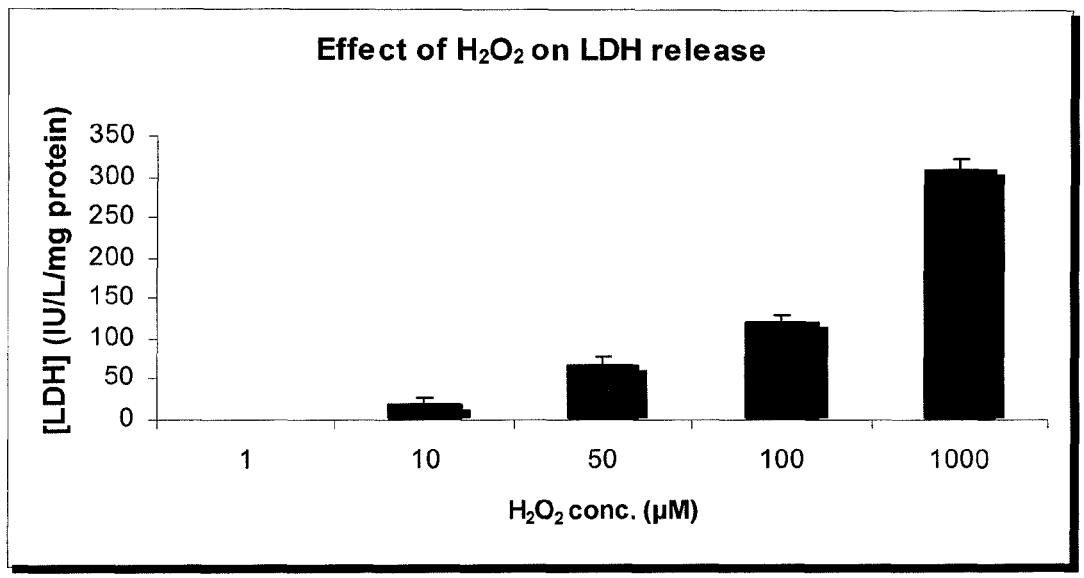
FIG. 6 is a graph showing lactate dehydrogenase (LDH) release in cultured human foetal astrocytes following exposure to different concentrations of hydrogen peroxide ($H_2O_2$). *$p<0.05$ compared to 0 μM $H_2O_2$ control, $p<0.05$ compared to 10 μM $H_2O_2$, *$p<0.05$ compared to 50 μM $H_2O_2$, $\psi<0.05$ compared to 100□μM $H_2O_2$.

LDH activity (a measure of cell death) was significantly increased in cultured human foetal astrocytes following exposure to 10-100 μM $H_2O_2$ for 20 min (FIG. 6) (*$p<0.05$ compared to 0 μM $H_2O_2$ control, $p<0.05$ compared to 10 μM $H_2O_2$, *$p<0.05$ compared to 50 μM $H_2O_2$, $\psi<0.05$ compared to 100 μM $H_2O_2$). The increase in LDH release directly correlated to the measured decrease in intracellular NAD levels (shown in FIG. 5).

Example 5

Antioxidants Inhibit Intracellular $NAD^+$ Depletion Induced by $H_2O_2$ in Human Foetal Astrocytes and Human Neuroblastoma Cells Oxygen radical induced stress can be ameliorated via effective antioxidant therapy. Quercetin is a plant derived polyphenolic compound with well demonstrated antioxidant activity. The ability of quercetin to modulate $H_2O_2$ induced NAD depletion in human foetal astrocytes was tested.

Figure 7:
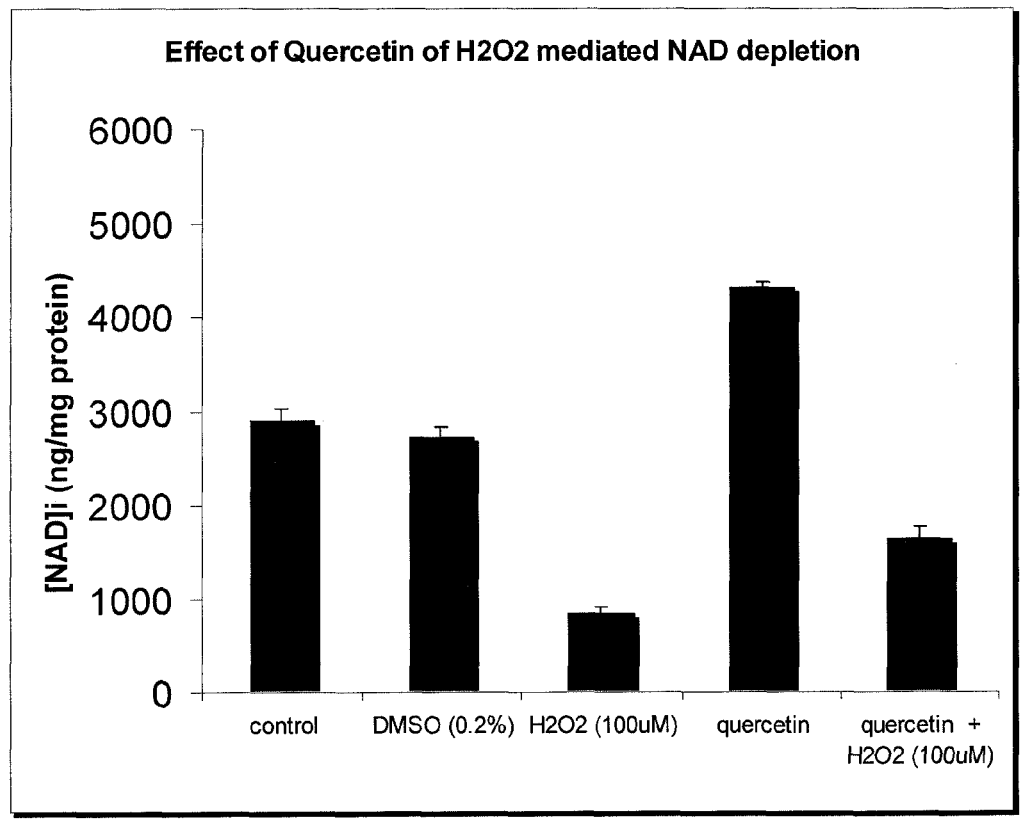
FIG. 7 is a graph showing the effect of quercetin on $H_2O_2$-mediated $NAD^+$ depletion in cultured human foetal astrocytes. *$p<0.05$, **$p<0.005$ compared to $H_2O_2$ alone.

Primary human foetal astrocytes were seeded into 24 well culture plates (~$10^5$ cells/well). Each well contained 1 ml of RPMI 1640 cell culture medium supplemented with 10% foetal bovine serum (FBS) and 0.5% Glutamix. Cultures were left to equilibrate for 24 hours before treatment with either DMSO (0.2%) alone or 0.2% DMSO+Quercetin (50 μM). After a further 24 hour incubation $H_2O_2$ was added to selected cultures (see FIG. 7) and incubated for 20 minutes at 37° C. in 5% $CO_2$ before being washed twice in PBS, followed by sonication in ~300 μL PBS. The resulting homogenates were placed on ice before immediate analysis of cellular $NAD^+$ levels as described in Example 1 above.

NAD⁺ levels were significantly preserved in cultured human foetal astrocytes when cultured in the presence of quercetin overnight followed by exposure to 10-100 μM $H_2O_2$ for 20 min (FIG. 7) (*$p<0.05$, **$p<0.005$ compared to $H_2O_2$ alone).

The effect of melatonin on NAD⁺ levels in human neuroblastoma cells was also investigated. Human neuroblastoma cells (SK-N-SH) were maintained in RPMI1640 cell culture medium supplemented with 10% foetal bovine serum, 2 mM I-glutamine, 1% penicillin/streptomycin, at 37° C. in a humidified atmosphere containing 95% air/5% $CO_2$. Before experimentation cells were seeded into 24 well culture plates to a density of approximately $5 \times 10^5$ cells and incubated overnight. On the day of the experiment, the culture medium was aspirated and discarded. Cells were washed twice with 500 μL PBS before addition of 1 ml PBS/well containing 10 μM iron, 10 μM ascorbic acid (to maintain iron in its $Fe^{2+}$ oxidation state), and 100 μM $H_2O_2$. The iron was incubated with the antioxidant Melatonin (2 μM-200 μM) for 5 mins before the addition of $H_2O_2$. All treatments were incubated for a further 30 mins at 37° C. in 5% $CO_2$. Cultures were then washed twice in PBS followed by sonication in ~300 μL PBS. The resulting homogenates were placed on ice before immediate analysis of cellular NAD⁺ levels as described in Example 1 above.

Figure 8:
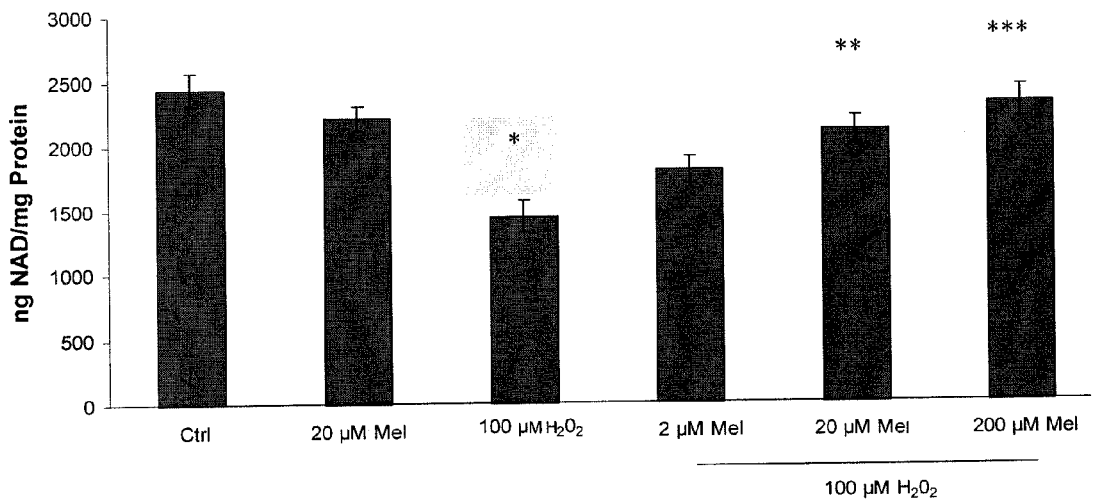
FIG. 8 is a graph showing the effect of $H_2O_2$ on intracellular $NAD^+$ levels in cultured human neuroblastoma cells following treatment with melatonin. *$p<0.05$ vs Ctrl, $p<0.05$ 100 μM $H_2O_2$ vs 20 μM Mel+$H_2O_2$, *$p<0.05$ 2 μM Mel+$H_2O_2$ vs 200 μM Mel+$H_2O_2$.

FIG. 8 shows that the depletion of intracellular NAD⁺ levels in cultured human neuroblastoma cells treated with 100 μM $H_2O_2$ is inhibited by pre-treatment with 2, 20 and 200 μM of melatonin (*$p<0.05$ vs Ctrl, $p<0.05$ 100 μM $H_2O_2$ vs 20 μM Mel+$H_2O_2$, *$p<0.05$ 2 μM Mel+$H_2O_2$ vs 200 μM Mel+$H_2O_2$).

Figure 9:
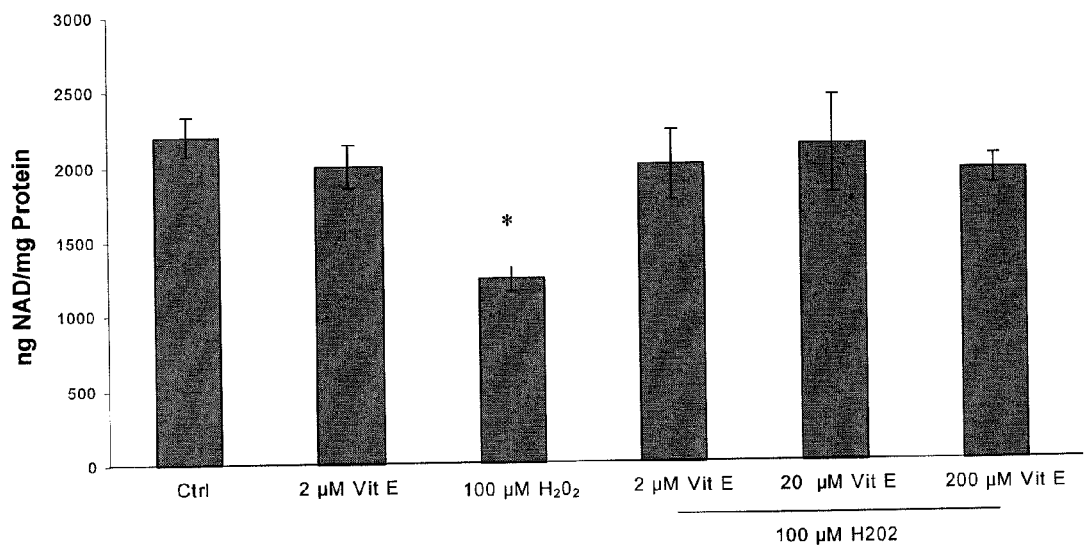
FIG. 9 is a graph showing the effect of $H_2O_2$ on intracellular $NAD^+$ levels in cultured human neuroblastoma cells following treatment with vitamin E. *$p<0.05$ vs Ctrl.

The effect of vitamin E on NAD⁺ levels in human neuroblastoma cells was also investigated. Human neuroblastoma cells (SK-N-SH) were maintained in RPMI 1640 cell culture medium supplemented with 10% foetal bovine serum, 2 mM I-glutamine, 1% penicillin/streptomycin, at 37° C. in a humidified atmosphere containing 95% air/5% $CO_2$. Before experimentation cells were seeded into 24 well culture plates to a density of approximately $5 \times 10^5$ cells and incubated overnight. On the day of the experiment, the culture medium was aspirated and discarded. Cells were washed twice with 500 μL PBS before addition of 1 ml PBS/well containing 10 μM iron, 10 μM ascorbic acid (to maintain iron in its $Fe^{2+}$ oxidation state), and 100 μM $H_2O_2$. The iron was incubated with the antioxidant Vitamin E (2-200 μM) for 5 mins before the addition of $H_2O_2$. All treatments were incubated for a further 30 mins at 37° C. in 5% $CO_2$. Cultures were then washed twice in PBS followed by sonication in ~300 μL PBS. The resulting homogenates were placed on ice before immediate analysis of cellular NAD⁺ levels as described in Example 1 above. FIG. 9 shows that the depletion of intracellular NAD⁺ levels in cultured human neuroblastoma cells treated with 100 μM $H_2O_2$ is inhibited by pre-treatment with 2, 20 and 200 μM vitamin E (*$p<0.05$ vs Ctrl).

These results demonstrate that oxidative stress induced NAD⁺ depletion can be ameliorated by treatment with antioxidants alone at effective doses.

Example 6

Clioquinol Reduces .OH-Induced NAD⁺ Depletion in Human Primary Astrocytes

Reaction of $H_2O_2$ with available redox active metal ions via Fenton chemistry leads to the generation of the hydroxyl radical (OH.).

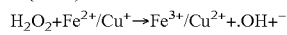

The increased oxidative modification of macromolecules in neurodegenerative disorders such as Alzheimer's disease appear to originate to a significant degree from increased intracellular production of the membrane permeable oxidant, hydrogen peroxide ($H_2O_2$) by inefficient mitochondria activity, increased extra-neuronal production of $H_2O_2$, activated microglia, and by Aβ deposits. This highly reactive free radical has the potential to induce significant DNA damage leading to PARP activation and NAD⁺ depletion.

The hypothesis that effective chelation of redox active metals such as $Fe^{2+}$ and $Cu^+$ would reduce .OH mediated PARP activation and subsequent NAD depletion was tested. Human neuroblastoma cells (SK-N-SH) were maintained in RPMI 1640 cell culture medium supplemented with 10% foetal bovine serum, 2 mM I-glutamine, 1% penicillin/streptomycin, at 37° C. in a humidified atmosphere containing 95% air/5% $CO_2$. Before experimentation cells were seeded into 24 well culture plates to a density of approximately $5 \times 10^5$ cells and incubated overnight. On the day of the experiment, the culture medium was aspirated and discarded. Cells were washed twice with 500 μL PBS before addition of 1 ml PBS/well containing 10 μM iron, 10 μM ascorbic acid (to maintain iron in its $Fe^{2+}$ oxidation state), and 100 μM $H_2O_2$. The iron was incubated with the chelator Clioquinol (1 μM-100 μM) for 5 minutes before the addition of $H_2O_2$. All treatments were incubated for a further 30 mins at 37° C. in 5% $CO_2$. Cultures were then washed twice in PBS followed by sonication in ~300 μL PBS. The resulting homogenates were placed on ice before immediate analysis of cellular NAD⁺ levels as described in Example 1 above.

Figure 10:
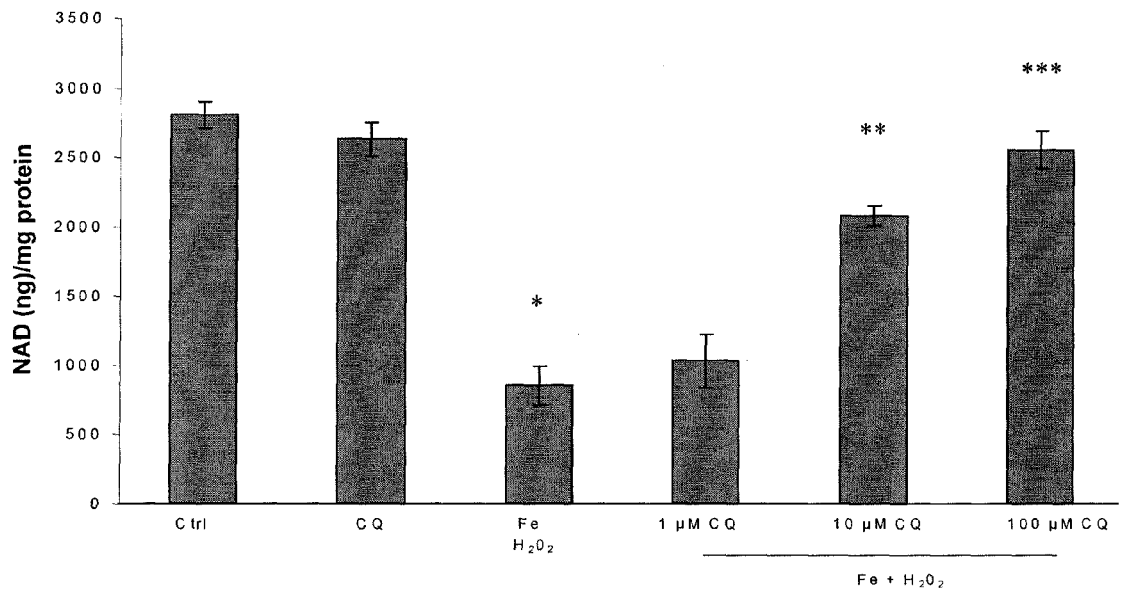
FIG. 10 is a graph showing the dose response effect of the lipophilic chelator clioquinol (CQ) on intracellular NAD concentrations in human neuroblastoma cells following treatment with $H_2O_2$ in the presence of ascorbic acid and ferrous iron. *$p<0.05$ vs Ctrl, $p<0.05$ vs $H_2O_2$+Fe, *$p<0.05$ vs 10 μM CQ+$H_2O_2$+Fe.

The dose response effect of the lipophilic chelator clioquinol (CQ) on intracellular NAD⁺ concentrations in human neuroblastoma cells treated with $H_2O_2$ is shown in FIG. 10 (*$p<0.05$ vs Ctrl, $p<0.05$ vs $H_2O_2$+Fe, *$p<0.05$ vs 10 μM CQ+$H_2O_2$+Fe). These results demonstrate that .OH-induced NAD⁺ depletion is effectively reduced by treatment with cell permeable chelating agents alone in a dose dependant fashion.

Example 7

Resveratrol Increases Intracellular NAD⁺

Primary human foetal astrocytes were seeded into 24 well culture plates (~$10^5$ cells/well). Each well contained 1 ml of RPMI 1640 cell culture medium supplemented with 10% foetal bovine serum (FBS) and 0.5% Glutamix. Cultures were left to equilibrate for 24 hours before treatment with resveratrol (100 μM). After a further 24 hour incubation, $H_2O_2$ was added to selected cultures and incubated for 20 minutes at 37° C. in 5% $CO_2$ before being washed twice in PBS. Followed by sonication in ~300 μL PBS. The resulting homogenates were placed on ice before immediate analysis of cellular NAD⁺ levels as described in Example 1 above.

Figure 11:
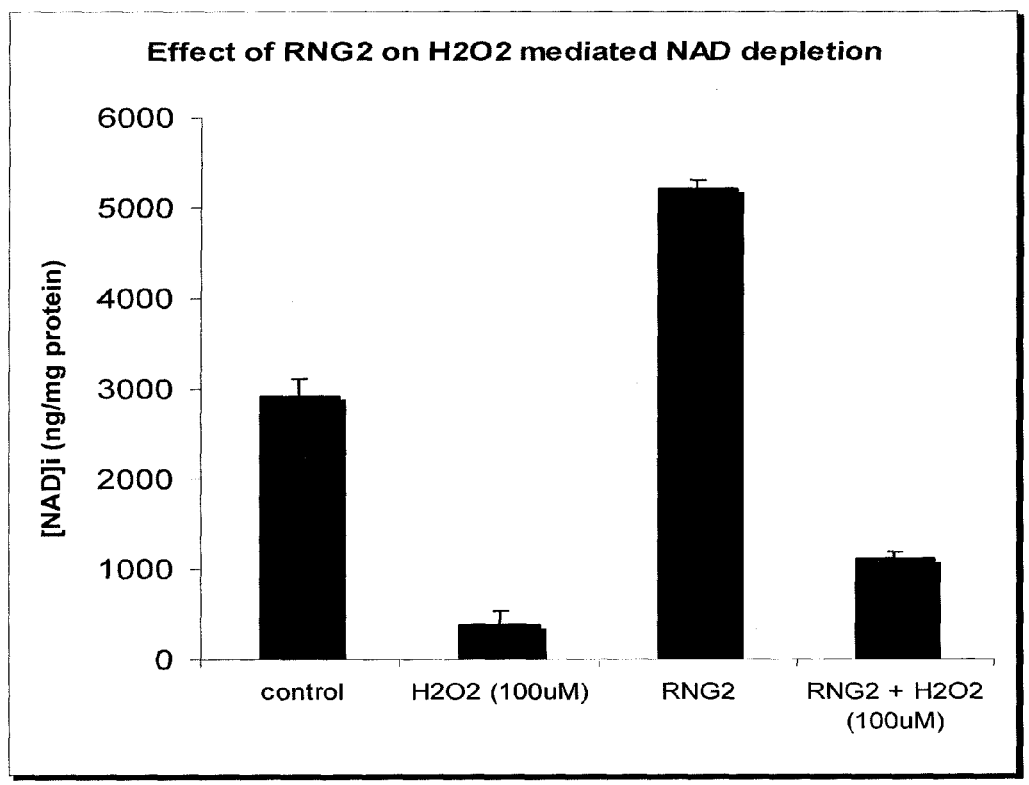
FIG. 11 is a graph showing the effect of resveratrol on $H_2O_2$-mediated $NAD^+$ depletion. Resveratrol significantly increased intracellular NAD+ above control (*p<0.05), **p<0.05 compared to $H_2O_2$ alone in human primary astrocytes.

Resveratrol significantly increased intracellular NAD⁺ above control levels (*$p<0.05$), **$p<0.05$ compared to $H_2O_2$ alone in human primary astrocytes (FIG. 11). While resveratrol showed only modest apparent antioxidant activity (small reduction in NAD⁺ depletion) the effect of resveratrol on intracellular NAD⁺ in cells not subject to oxidative stress was marked, showing an approximately 75% increase in intracellular NAD⁺ concentration. While modest increases in NAD⁺ levels above untreated controls have been observed with other antioxidants due to reduced constitutive oxidative activity, the effect of resveratrol was 100% greater than the best of these other antioxidants. Example 8: Resveratrol increases intracellular NAD$^+$ in the presence the IDO inhibitor 1-MT or the QPRT inhibitor PA in primary cells Primary human foetal astrocytes were seeded into 24 well culture plates (~10$^5$ cells/well). Each well contained 1 ml of RPMI 1640 cell culture medium supplemented with 10% foetal bovine serum (FBS) and 0.5% Glutamix. Cultures were left to equilibrate for 24 hours before treatment with resveratrol (100 µM), 1-MT (1 mM), PA (1 mM), resveratrol (100 µM)+1-MT (1 mM), and resveratrol (100 µM)+PA (1 mM) After a further 24 hour incubation cells were washed twice in PBS, followed by sonication in ~300 µL PBS. The resulting homogenates were placed on ice before immediate analysis of cellular NAD$^+$ levels as described in Example 1 above.

Figure 12:
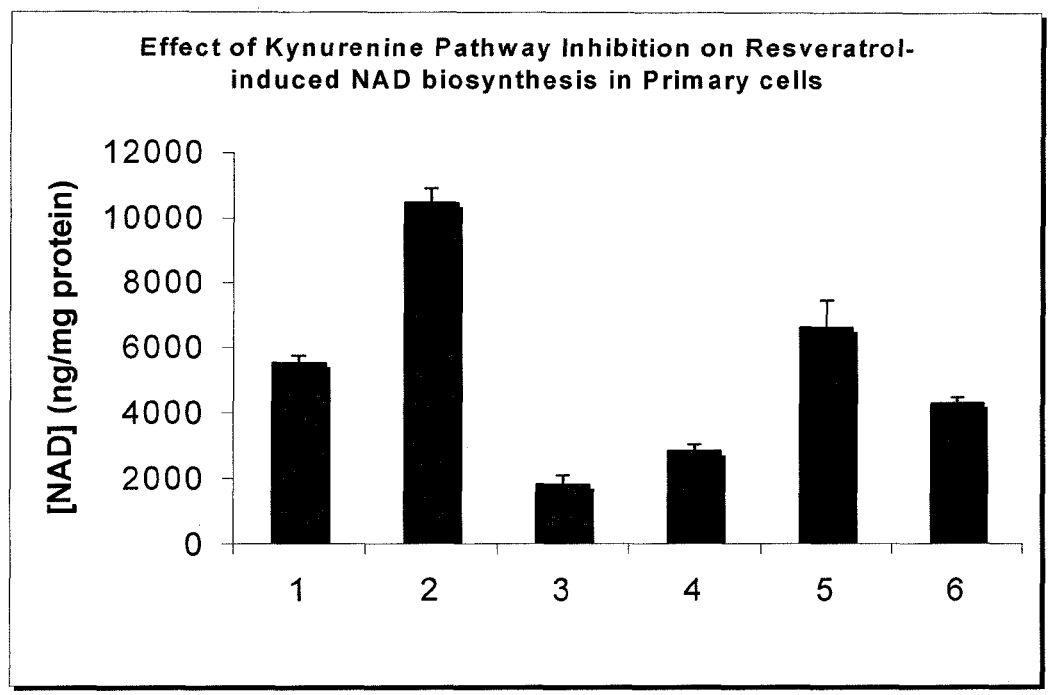
FIG. 12 is a graph showing the effect of the kynurenine pathway inhibitor 1-MT on resveratrol-induced $NAD^+$ synthesis via the de novo pathway.
Figure 13:
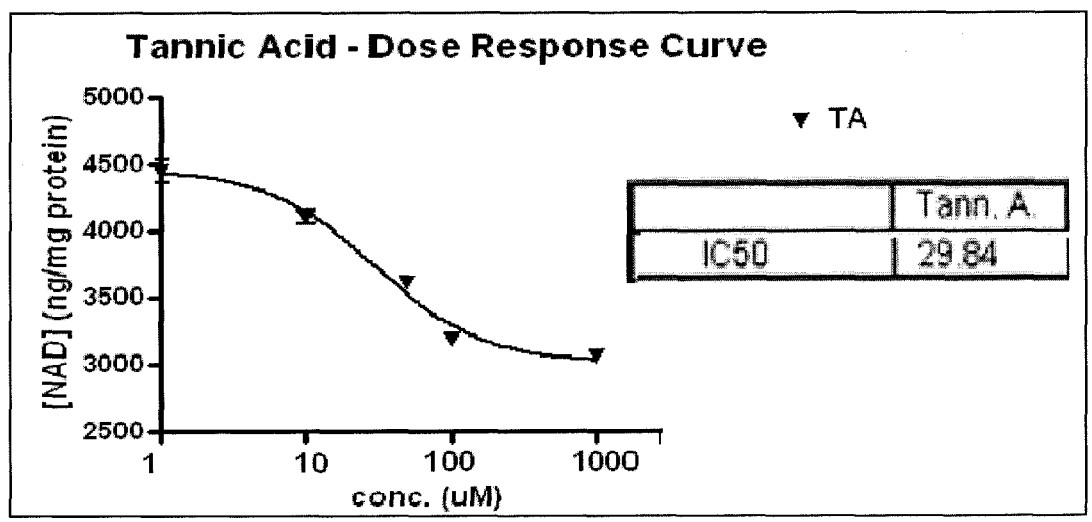
FIG. 13 is a graph of a dose response curve showing the effect of the nicotinamide mononucleotide adenylyl transferase (NMNAT) inhibitor tannic acid on $NAD^+$ synthesis. IC=inhibitory concentration.

The effect of resveratrol on intracellular NAD$^+$ levels either alone or in the presence of 1-MT, 1 mM (an inhibitor of IDO, the first enzyme in de novo NAD synthesis) and PA 1 mM, (an inhibitor of QPRT, a downstream enzyme in de novo NAD synthesis) (FIG. 12) (*p<0.05 compared to 1-MT treatment alone, **p<0.05 compared to PA treatment alone). Both inhibitors were used at concentrations considered to completely block the activity of their respective enzymes. Neither inhibitor was able to abrogate the resveratrol effect suggesting that resveratrol may be able to induce NAD$^+$ synthesis via the salvage pathway.

Example 9

The NMNAT Inhibitor Tannic Acid Abrogates Resveratrol-Mediated Increases in Intracellular NAD$^+$ Around 5 enzymes are used by the salvage pathway (see FIG. 1) to generate NAD$^+$ from various sources, including nicotinamide mononucleotide adenylyl transferase (NMNAT). NMNAT was inhibited and its effect was evaluated in reference to the previously observed increase in intracellular NAD$^+$ levels caused by resveratrol. Primary human foetal astrocytes were seeded into 24 well culture plates (~10$^5$ cells/well). Each well contained 1 ml of RPMI1640 cell culture medium supplemented with 10% foetal bovine serum (FBS) and 0.5% Glutamix. Cultures were left to equilibrate for 24 hours before treatment with tannic acid (100 µM) or resveratrol (100 µM) or resveratrol (100 µM)+tannic acid (100 µM). Cultures were incubated for a further 24 hours at 37° C. in 5% CO$_2$ before being washed twice in PBS, followed by sonication in ~300 µL PBS. The resulting homogenates were placed on ice before immediate analysis of cellular NAD$^+$ levels as described in Example 1 above.

Figure 14:
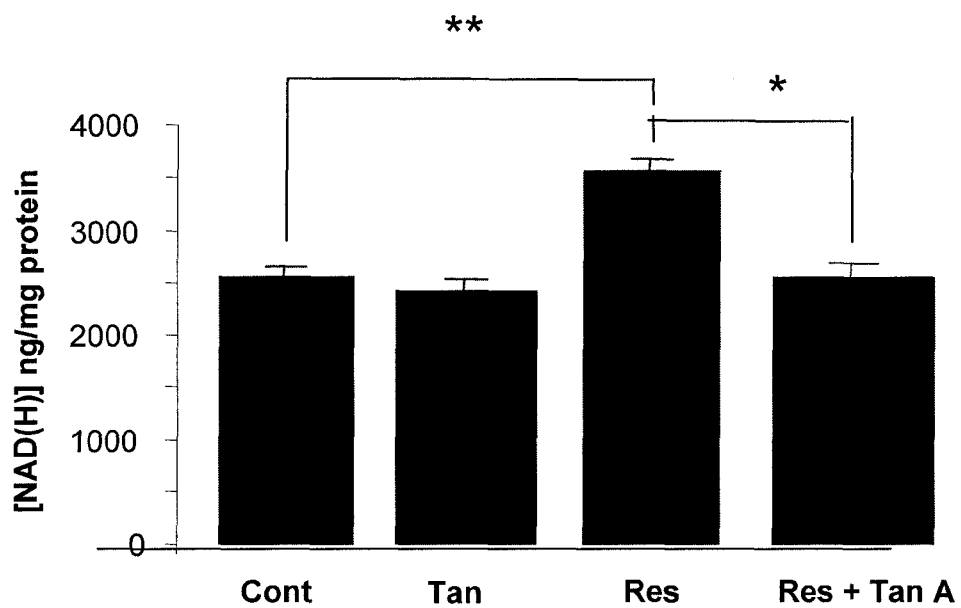
FIG. 14 is a graph showing the effect of the nicotinamide mononucleotide adenylyl transferase (NMNAT) inhibitor tannic acid on resveratrol-mediated $NAD^+$ synthesis. *p<0.05 compared to resveratrol treatment alone. **p<0.05 compared to control.

Treatment with tannic acid (24 hours, 100 µM) completely abrogated the effect of resveratrol on intracellular NAD$^+$ levels (FIG. 14). Treatment with tannic acid alone (100 µM) did not significantly reduce NAD$^+$ levels over the 24 hour incubation period. (FIG. 14) (*p<0.05 compared to resveratrol treatment alone, **p<0.05 compared to control). These results indicate that complete inhibition of NMNAT by tannic acid was able to prevent the previously observed resveratrol-mediated increase in intracellular NAD$^+$. The increase in intracellular NAD$^+$ levels in the presence of resveratrol may therefore be best explained by an up-regulation in NMNAT activity.

Example 10

Resveratrol Increases NMNAT Activity in Human Brain Astrocytes

Figure 15:
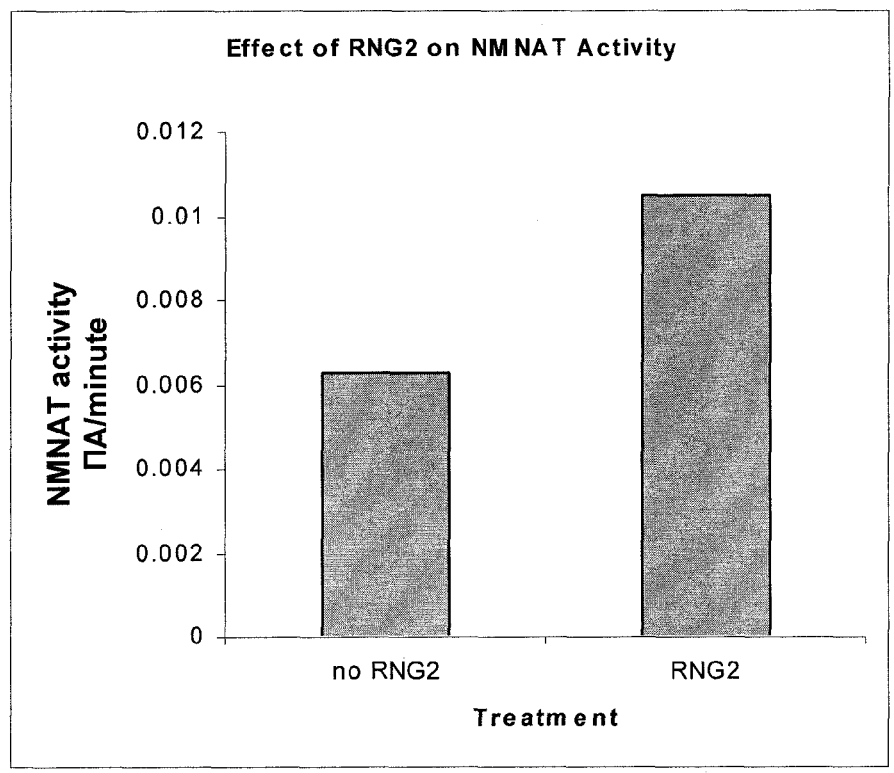
FIG. 15 is a graph showing the effect of resveratrol on nicotinamide mononucleotide adenylyl transferase (NMNAT) activity in human brain astrocytes.

The effect of resveratrol on NMNAT activity in whole cell homogenates of human astrocytes is shown in (FIG. 15). Human brain astrocytes were trypsonised, washed twice, and then resuspended in HEPES buffer before being homogenised by shorts bursts of sonication. Cellular particulates were then removed by centrifugation and the supernatant was used for NMNAT activity analysis. 200 µM resveratrol was added to a small volume of supernatant. NMNAT activity was then determined in this sample and a sample without resveratrol (control) using a protocol modified from Balducci et al. Anal. Biochem. (1995). 228: 64-68. The standard assay was performed at 37° C. in a 1 ml, 1 cm path curvette in a final volume of 850 µl. The reaction mixture contained 240 µl HEPES (10 mM, pH 7.4) containing 390 µl ethanol reagent, MgCl$_2$ (40 mM), 100 µl ATP (12.5 mM), 50 µl ADH (0.5 mg/ml), and the appropriate amount of hr-NMNAT1. The reaction was started by adding nicotinamide mononucleotide (NMN) to a final concentration of 0.625 mM. The increase in absorbance for 10 minutes was recorded continuously at 340 nm using the Cary 50BIO UV spectrophotometer (Varian, Sydney). Change in absorbance per minute was calculated from the slope of the linear progress curve and the amount of NADH produced per minute (nM/min) was determined using an NADH standard curve.

Figures 16, 17:
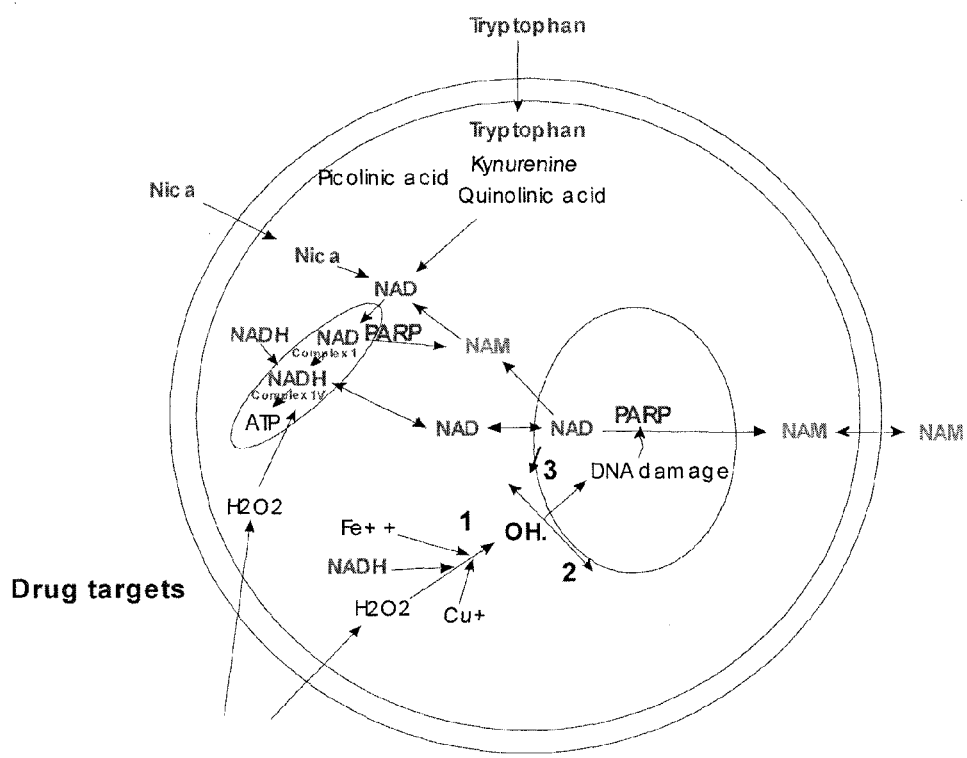
FIG. 16 is a table showing the effect of various concentrations of resveratrol on the activity of nicotinamide mononucleotide adenylyl transferase (NMNAT) activity in human brain astrocytes.
FIG. 17 is a diagram showing a mechanism common by which oxidative stress induces DNA damage.

Treatment with 200 µM resveratrol increased NMNAT activity in whole cell homogenates of human brain astrocytes by 67% compared to control (no resveratrol treatment). The effect of resveratrol on the activity of NMNAT was confirmed directly using human recombinant NMNAT (hrNMNAT: Alexis Biochemicals) (FIG. 16). The presence of resveratrol significantly increased NMNAT activity in the whole cell extract by approximately 70% (FIG. 16). Resveratrol dose dependently increased Vmax by >500% and decreased the Km by approximately 3 times. The standard assay was performed at 37° C. in a 1 ml, 1 cm path cuvette in a final volume of 850 µl. The reaction mixture contained 240 µl HEPES (10 mM, pH 7.4) containing 390 µl ethanol reagent, MgCl$_2$ (40 mM), 100 µl ATP (12.5 mM), 50 µl ADH (0.5 mg/ml), and the appropriate amount of hr-NMNAT1. The reaction was started by adding NMN to a final concentration of 0.62 mM. NMNAT activity was measured for resveratrol (50 µM, 100 µM and 200 µM). The increase in absorbance for 10 minutes was recorded continuously at 340 nm using the Cary 50BIO UV spectrophotometer (Varian, Sydney). Change in absorbance per minute was calculated from the slope of the linear progress curve and the amount of NADH produced per minute (nM/min) was determined using an NADH standard curve.

These results strongly suggest that resveratrol is acting directly on the NAD salvage pathway enzyme NMNAT most likely through an as yet unidentified allosteric up-regulation of enzyme activity.

Example 11

Clioquinol and Vitamin E Reduce NAD$^+$ Depletion in Neuroblastoma Cells Exposed to H$_2$O$_2$ and Fe Human neuroblastoma cells (SK-N-SH) were maintained in RPMI 1640 cell culture medium supplemented with 10% foetal bovine serum, 2 mM l-glutamine, 1% penicillin/streptomycin, at 37° C. in a humidified atmosphere containing 95% air/5% CO$_2$. Before experimentation cells were seeded into 24 well culture plates to a density of approximately 5×10$^5$ cells and were incubated overnight before experimentation. On the day of the experiment, the culture medium was aspirated and discarded. Cells were then washed twice with 500 µL DPBS before addition of 1 ml DPBS/well containing 10 µM iron or copper, 10 µM ascorbic acid (to maintain iron in its $Fe^{2+}$ oxidation state), and 100 µM $H_2O_2$. The iron was incubated with the chelator clioquinol (CQ) and/or 20 µM of the antioxidant vitamin E (VitE) for 5 mins before the addition of $H_2O_2$. All combinations were incubated for 30 mins before $NAD^+$ assays were performed as described in Example 1 above.

Figure 18:
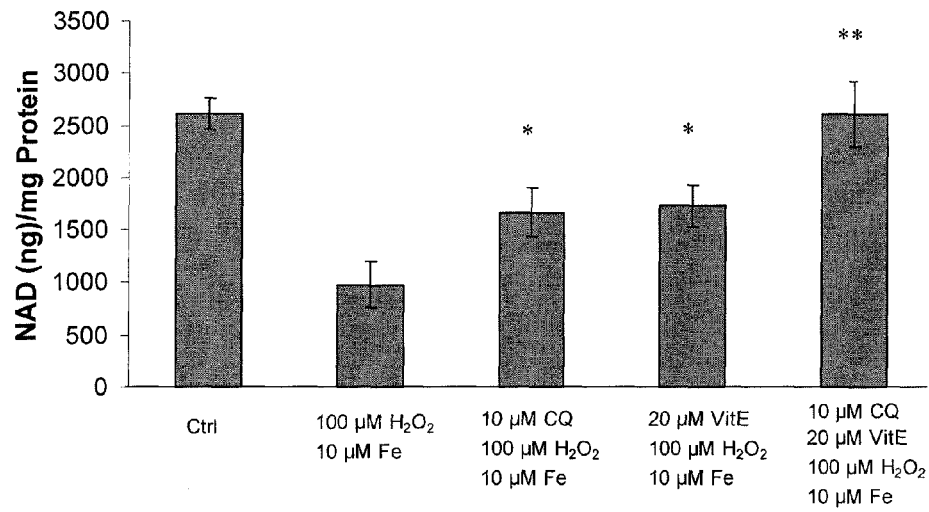
FIG. 18 is a graph showing $NAD^+$ production in neuroblastoma cells treated with chelators (clioquinol—CQ) and an antioxidant (vitamin E) after exposure to the pro oxidant ($H_2O_2$) and iron (Fe)

Treatment with the chelator, clioquinol, and the antioxidant, Vitamin E, produced a synergistic protection against free radical induced $NAD^+$ depletion in neuroblastoma cells (FIG. 18).

Example 12

Effect of U.V. Radiation+/−Supplementation on Intracellular NAD and Extracellular LDH Activity in Cultures of Human Skin Cells (Keratinocytes, Fibroblasts)

Human skin cells (keratinocytes) were grown at a density of $5 \times 10^6$ in PERMANOX® chamber-slides (NUNC) for 2 weeks. This method is commonly used in the industry and is well known to those skilled in the art. Accordingly, there is no need to detail the method utilised in this specification.

Figure 19A:
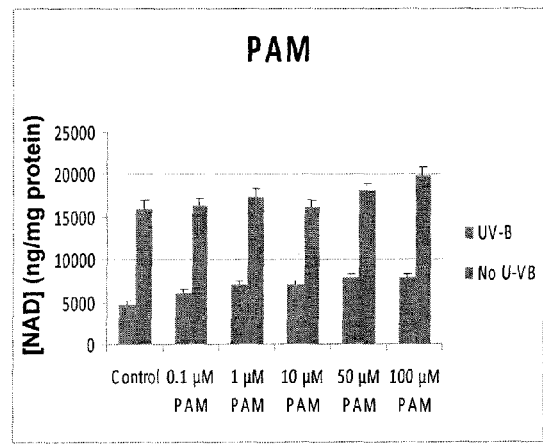
FIGS. 19a-d show graphical representations of intracellular NAD concentrations+/−UV exposure, +/−supplementation.
Figure 19B:
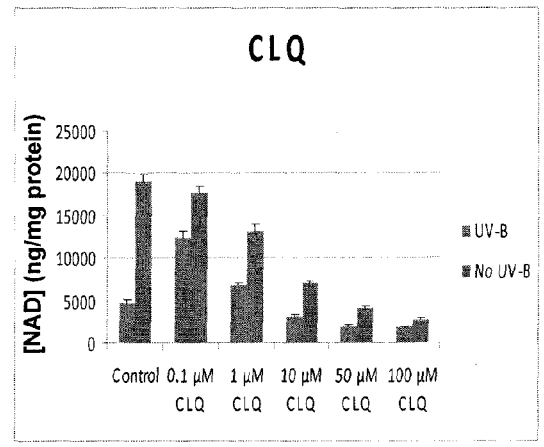
Figure 19C:
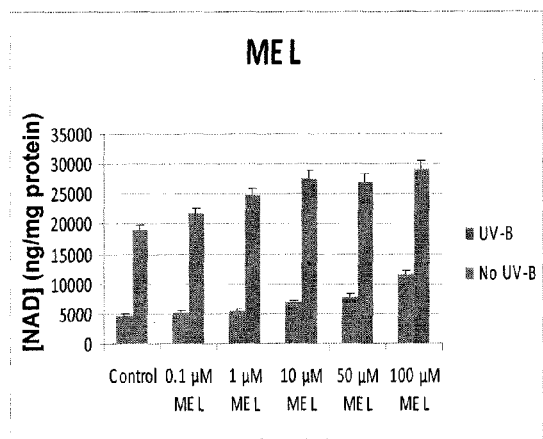
Figure 19D:
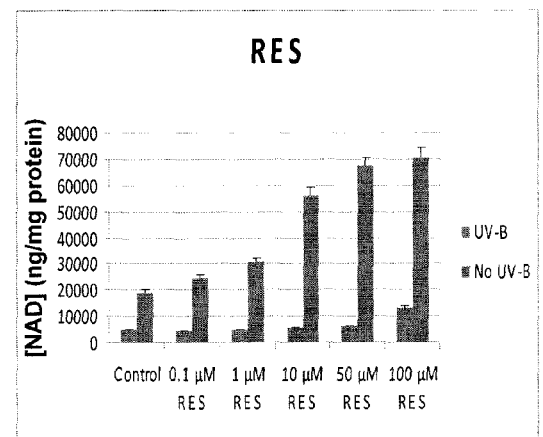
Figure 19E:
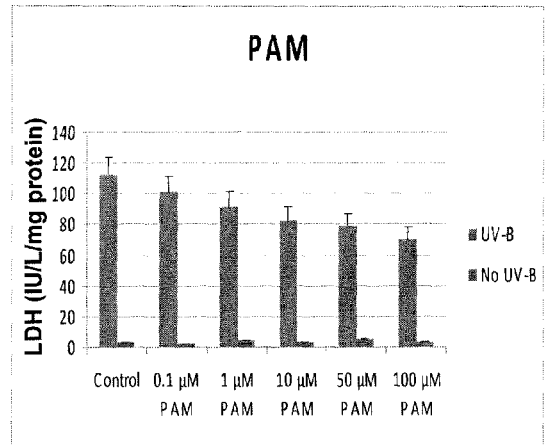
FIGS. 19e-h show graphical representations of supernatant LDH activity+/−UV exposure, +/−supplementation.
Figure 19F:
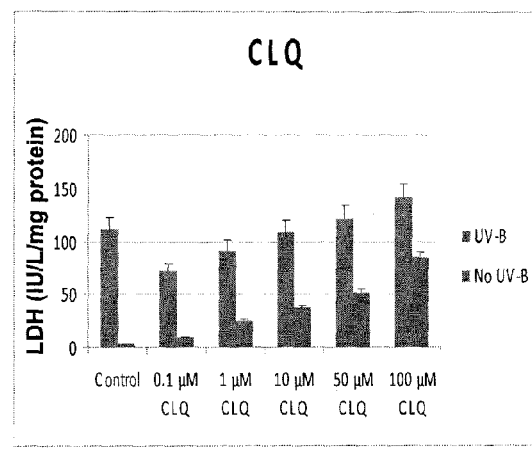
Figure 19G:
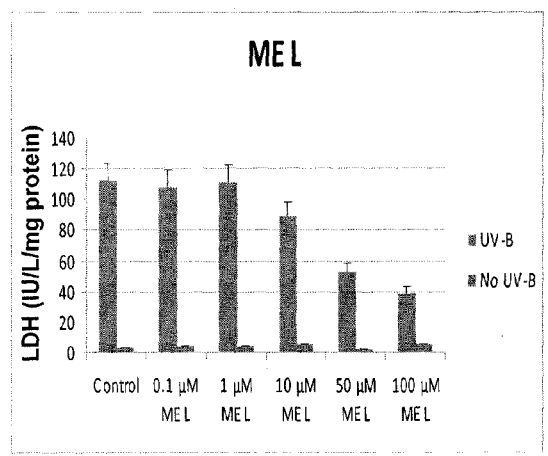
Figure 19H:
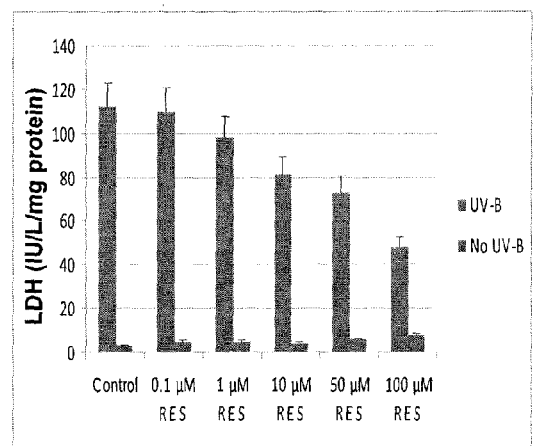

Cells were either left unexposed or exposed to 15 min UVB ($\sim$200 $mJcm^{-2}$). The culture medium was then supplemented with either 0.1-100 µM Clioquinol (CLQ) (FIG. 19a), Picolinamide (PAM) (FIG. 19b), Melatonin (MEL) (FIG. 19c) or Resveratrol (RES) (FIG. 19d) as single therapy for 24 hrs.

Figure 21:
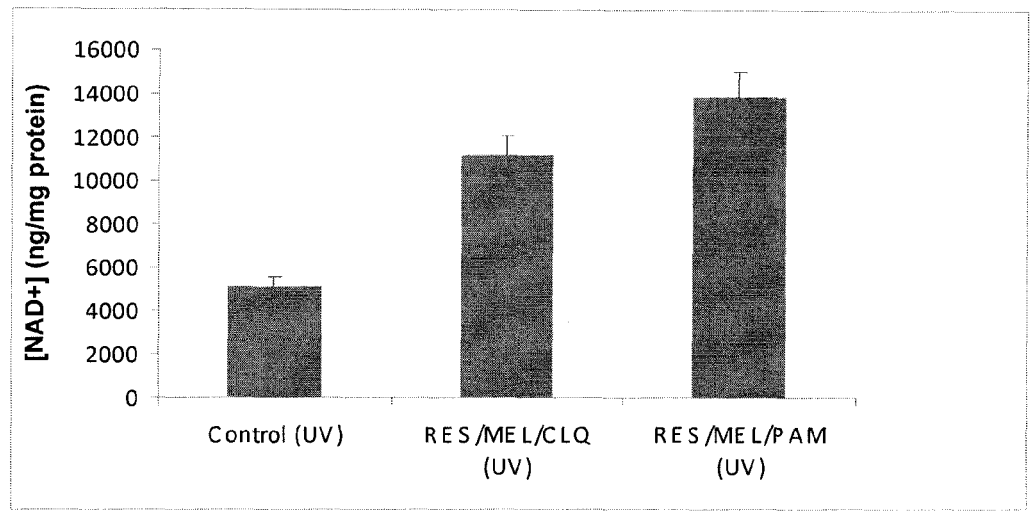
FIG. 21 is a graph showing the effect of triple supplementation (selected combinations) on NAD concentrations following treatment with RES+MEL+CLQ or RES+MEL+PAM on NAD recovery 24 hr after UVB exposure, in human primary Keratinocytes.

Cells were left to incubate for 24 hrs before analysis of intracellular NAD (FIG. 19a-d to FIG. 21) and extracellular LDH (FIG. 21). FIGS. 19a-d show the intracellular NAD concentrations+/−UV exposure, +/−supplementation. FIGS. 19e-h show supernatant LDH activity+/−UVE exposure, +/−supplementation.

FIGS. 19a-d show that NAD levels are significantly reduced, and LDH activity in the supernatant (indicating cell death, FIGS. 19e-h) is correspondingly increased in human fibroblasts exposed to UVB radiation. Minimum effective concentrations (MEC) for each therapeutic were: 0.1 µM MEL, 0.1 µM CLQ, 10 µM MEL and 50 µM RES, (N=3 for each treatment group).

Figure 20A:
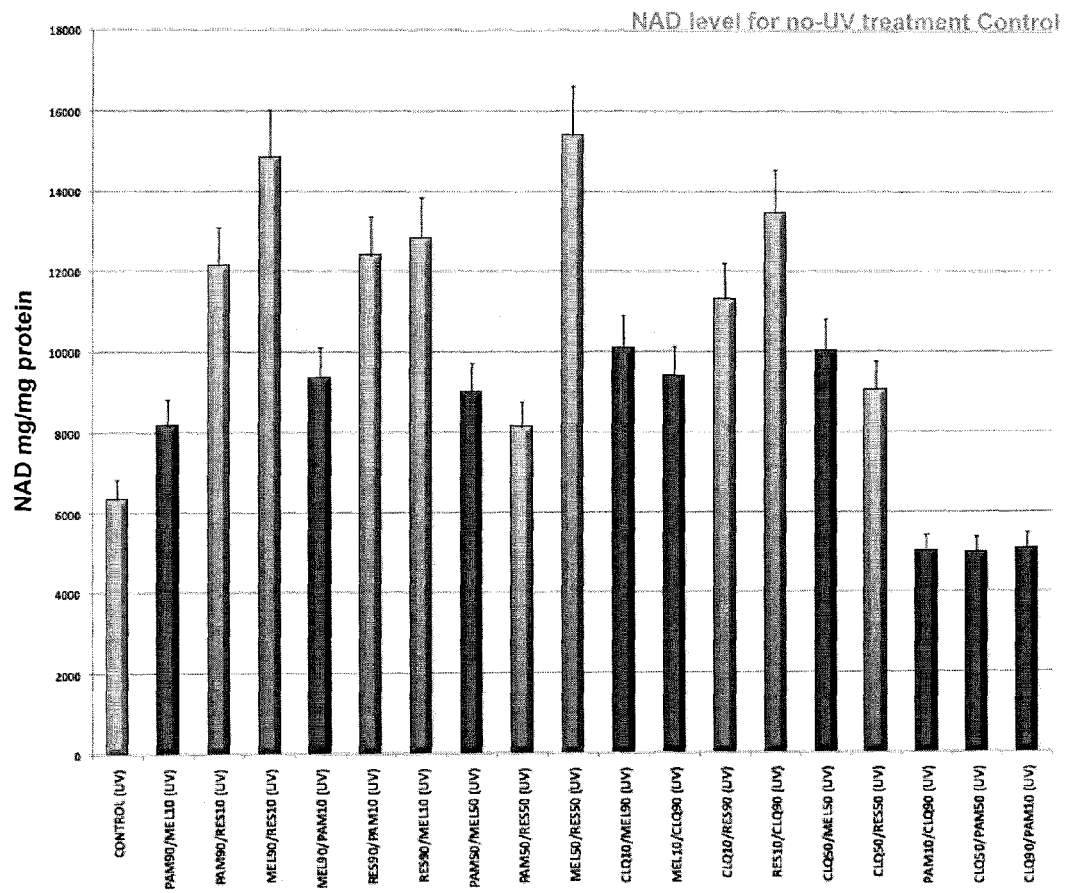
FIG. 20a is a graph showing the effect of dual supplementation on NAD concentrations following treatment with RES+/−PAM+/−CLQ+/−MEL on NAD recovery 24 hr after UVB exposure, in human primary Keratinocytes.
Figure 20B:
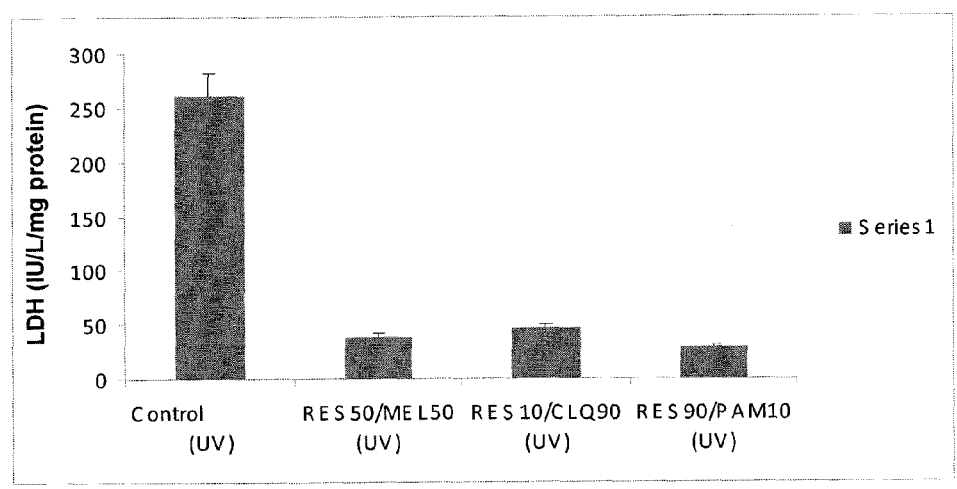
FIG. 20b is a graph showing the effect of dual supplementation on LDH release (cell death) following treatment with RES+MEL or RES+CLQ or RES+PAM for 24 hr after UVB exposure, in human primary Keratinocytes.

FIGS. 20a and 20b show that, in general, dual therapies containing RES are much more successful in regenerating intracellular NAD and minimising overall cell death (LDH activity) compared any other dual combination. Importantly selected dual therapy combinations were able to return NAD levels and reduce cell death (LDH activity) to no-UV treatment control levels. FIG. 20a shows the effect of dual supplementation on NAD concentrations following treatment with RES+/−PAM+/−CLQ+/−MEL on NAD recovery 24 hr after UVB exposure, in human primary Keratinocytes. The lighter shade bars (in greyscale) represent treatment containing RES. FIG. 20b shows the effect of dual supplementation on LDH release (cell death) following treatment with RES+MEL or RES+CLQ or RES+PAM for 24 hr after UVB exposure, in human primary Keratinocytes. FIG. 21a also shows that triple therapy with RES/MEL/PIC was able to return NAD levels and reduce cell death (LDH activity) to no-UV treatment control levels. FIG. 21 shows the effect of triple supplementation (selected combinations) on NAD concentrations following treatment with RES+MEL+CLQ or RES+MEL+PAM on NAD recovery 24 hr after UVB exposure, in human primary Keratinocytes. For each therapeutic supplement a concentration equal to its $EC_{33}$ was used for the triple combination.

Example 13

Effect of U.V. Radiation on DNA Damage and Repair in Human Skin Cells (Keratinocytes, Fibroblasts)

Human skin cells (keratinocytes and fibroblasts) were grown at a density of $5 \times 10^6$ in PERMANOX® chamber-slides (NUNC) for 2 weeks. This method is commonly used in the industry and is well known to those skilled in the art. Accordingly, there is no need to detail the method utilised in this specification.

Cells were exposed to 15 min UVB ($\sim$200 $mJcm^{-2}$). The culture medium was then supplemented with any of the following:

100 µM Clioquinol (C), 100 µM Picolinamide (P), 100 µM Melatonin (M) or 100 µM Resveratrol (R) as single therapy;

10 µM (R)+50 µM (M), 10 µM (R)+0.1 µM (C) or 90 µM (R)+0.08 µM (P) as dual therapy; or 0.65 µM (P)+33 µM (C)+5 µM (R) or 0.3 µM (P)+33 µM (C)+5 µM (R) as triple therapy.

All doses used for single therapy were equivalent to $IC_{100}$ for each therapeutic, whilst optimum dose combinations used for dual therapy were $\{IC_{50}\ (R)+IC_{50}\ (M)\}$, $\{IC_{10}\ (R)+IC_{90}\ (C)\}$, $\{IC_{90}\ (R)+IC_{10}\ (P)\}$ and the optimum dose combinations for the triple therapy were $\{IC_{33}\ (R)+IC_{33}\ (M)+IC_{33}\ (C)\}$, $\{IC_{33}\ (R)+IC_{33}\ (M)+IC_{33}\ (P)\}$.

Figure 22B:
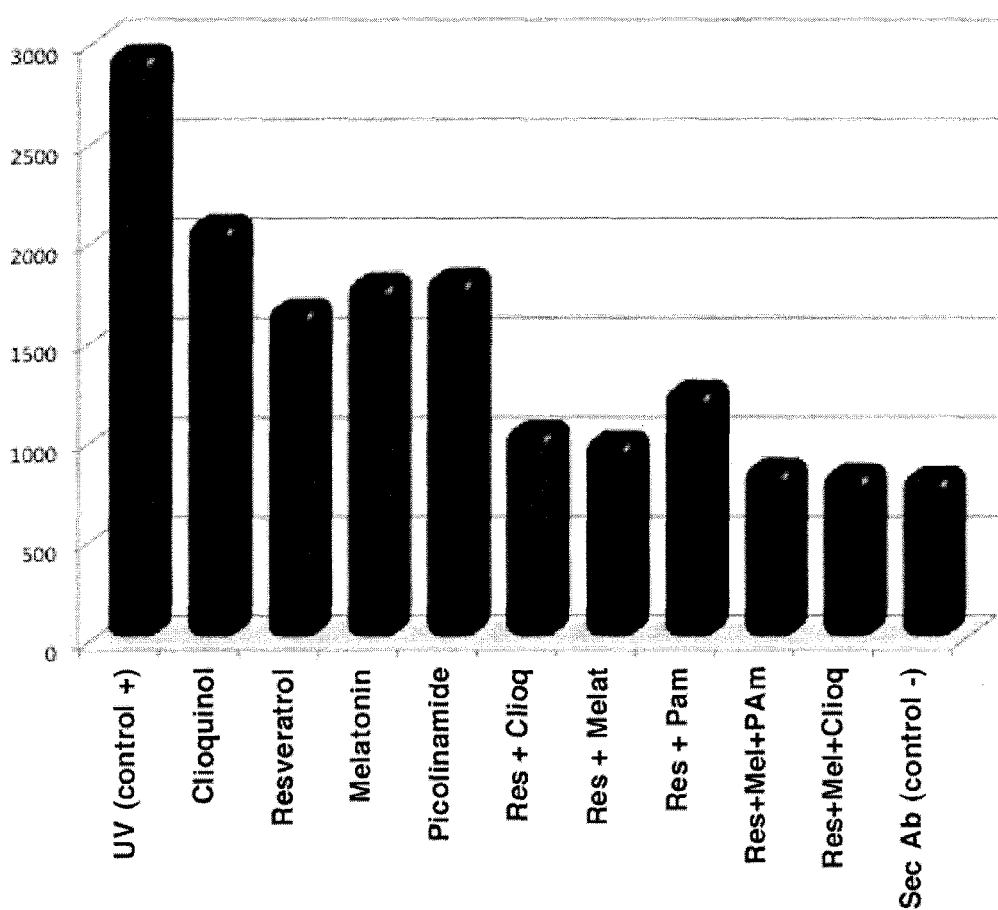
FIG. 22b is a graph showing the semiquantitation of fluorescent intensities for each of the ICC stained sections of Keratinocytes.
Figure 22A:
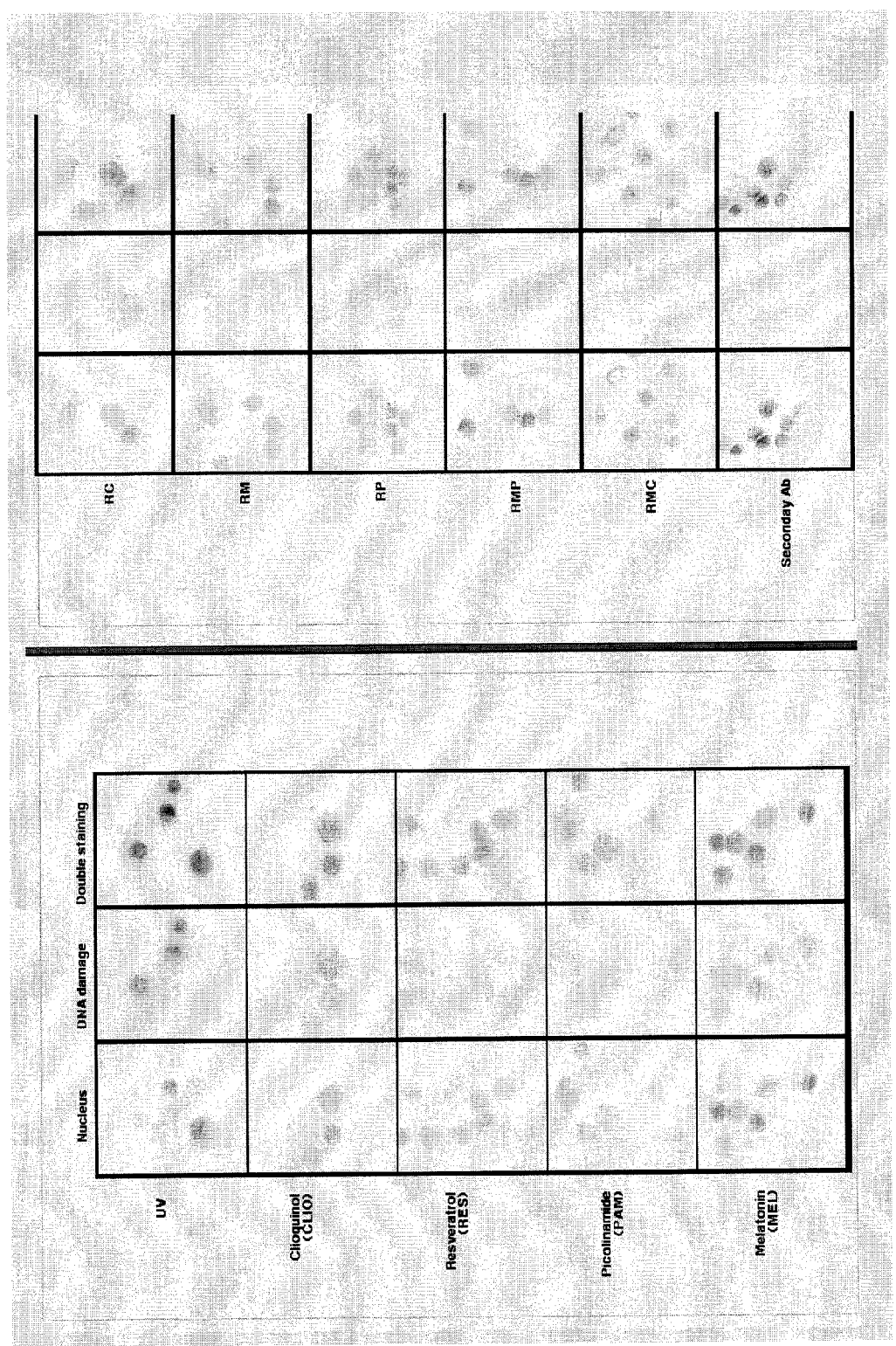
FIG. 22a is an immunocytochemistry visualisation of Keratinocytes depicting intense staining for DNA damage (middle column) for UV treated cells without supplementation.
Figure 23A:
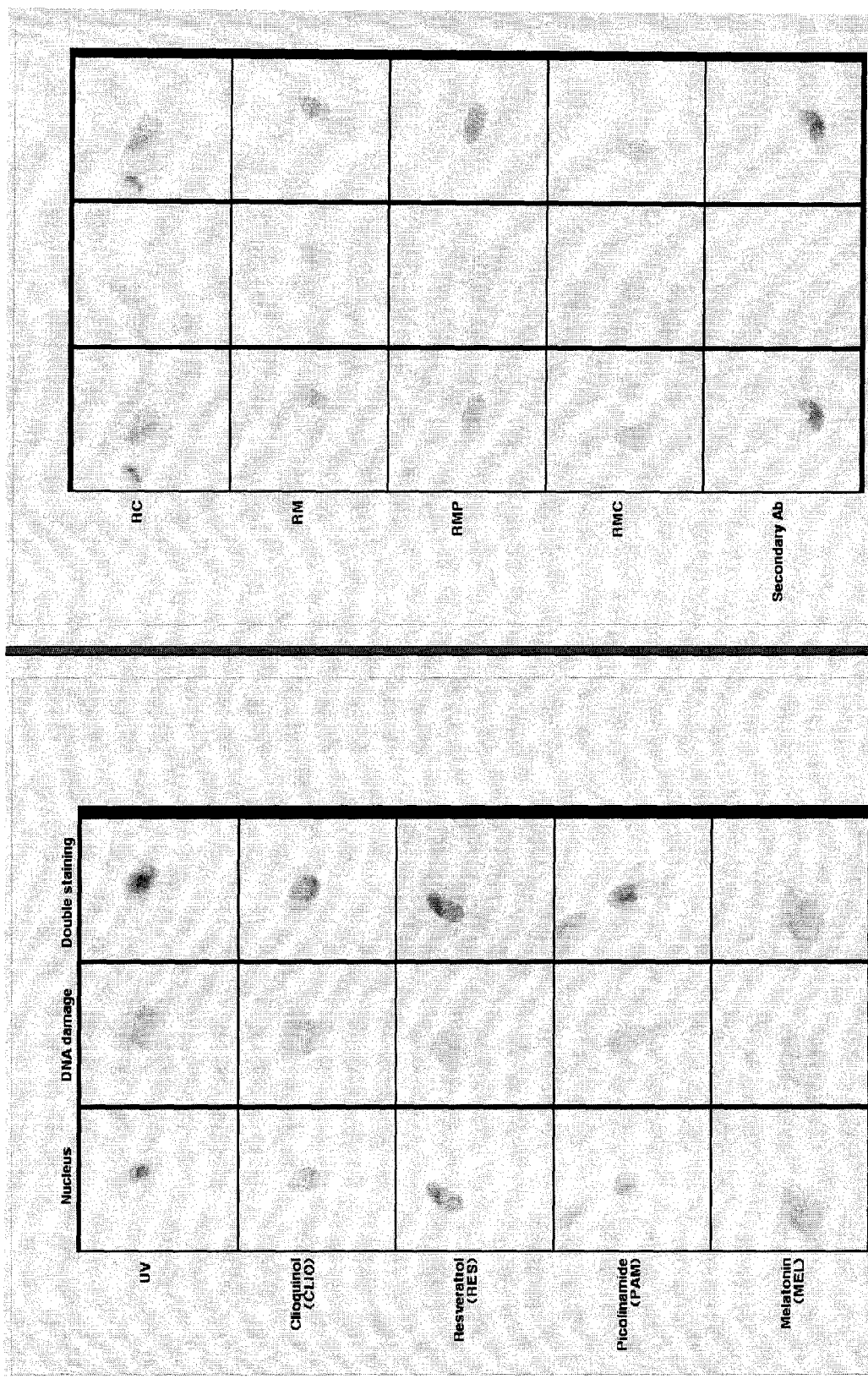
FIG. 23a is an immunocytochemistry visualisation of Fibroblasts depicting intense staining for DNA damage (middle column) for UV treated cells without supplementation.
Figure 23B:
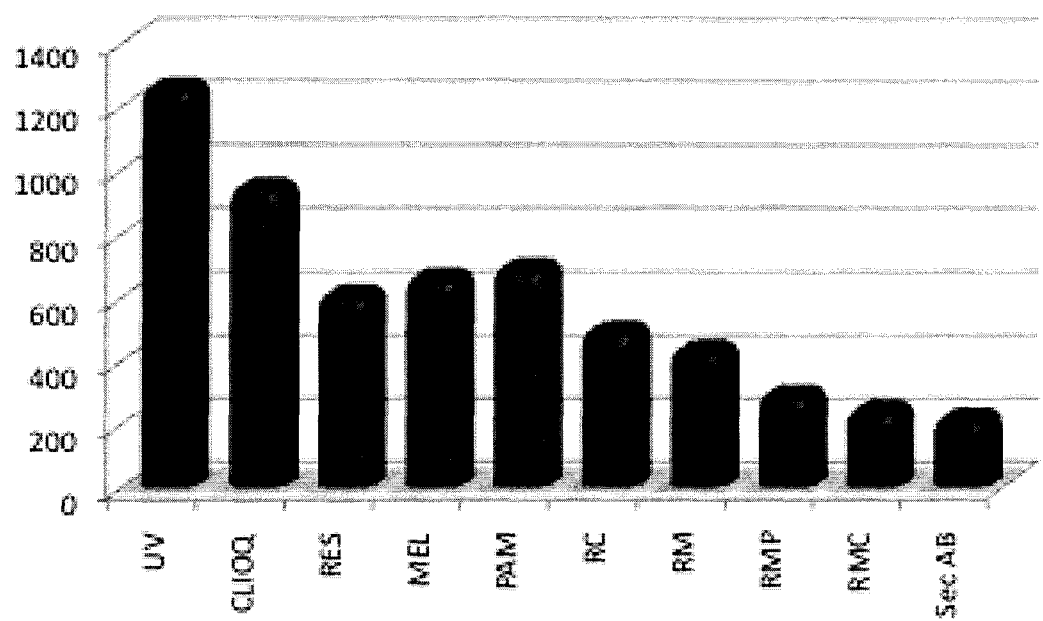
FIG. 23b is a graph showing the semiquantitation of fluorescent intensities for each of the ICC stained sections of Fibroblasts.

Cells were left to incubate for 24 hrs before analysis of DNA damage (see FIGS. 22a and 22b for Keratinocytes and FIGS. 23a and 23b for Fibroblasts).

For Immunocytochemistry visualisation and semi quantitation, cells were fixed with acetone/methanol (vol/vol) for 20 min at −20° C. Cells were then rinsed 3 times with PBS and a gentle membranous permeabilization was performed by incubation with 0.025% Triton X 100 in PBS for 10 min at room temperature. After washing, cells were incubated with 5% normal goat serum (NGS) in PBS for 45 min at room temperature, rinsed twice with PBS and incubated for 1 h at 37° C. with the primary antibody 6-4 PP mAb (Cosmo Bio Ltd, Japan) diluted in 5% NGS. Cells were then washed with 5% NGS solution and incubated for 1 h at 37° C. with the appropriate labelled secondary antibodies (goat anti-mouse IgG coupled with Alexa 594). Nuclear staining was performed using DAPI at 1 µg/ml for 5 min at room temperature. After several washings with PBS at 37° C., the cover slips were quickly mounted on glass slides with Fluoromount-G, and examined using an Olympus BX60 fluorescence microscope associated with a digital SensiCam. The following three controls were performed for each labelling experiment: 1) isotypic antibody controls for mAbs and serum control for pAbs, 2) incubation with only the secondary labelled antibodies, 3) estimation of auto-fluorescence of unlabelled cells. Intensity has been quantified (semi-quantification) using ImageJ 10.2. Three individual microscopic fields were analysed for each treatment and the SEM for the data was determined to be <5%.

FIGS. 22a and 23a show intense staining for DNA damage (middle column) for UV treated cells without supplementation. The intensity of the DNA damage signal was slightly weaker for single therapy, weaker still for dual therapy and no different to -ve control (i.e. no UV damage) in cells treated with triple therapy (N=3, Keratinocytes, N=1 Fibroblasts for each treatment group). Note that maximum effective single therapies ($IC_{100}$) were not as effective as $IC_{100}$ equivalent dual therapies that were in turn not as effective as $IC_{100}$ equivalent triple therapies.

FIGS. 22b and 23b show the semiquantitation of fluorescent intensities for each of the ICC stained sections indicating strong graphical evidence for triple therapy producing the most effective DNA repair.

Example 14

Effect of U.V. Radiation+/−Supplementation on DNA Repair in Cultures of Human Skin Cells (Fibroblasts)

Human skin cells (Fibroblasts) were grown at a density of $5 \times 10^6$ in PERMANOX® chamber-slides (NUNC) for 2 weeks. This method is commonly used in the industry and is well known to those skilled in the art. Accordingly, there is no need to detail the method utilised in this specification.

Cells were either left unexposed or exposed to 15 min UVB (~200 mJcm$^{-2}$). The culture medium was then supplemented with either 100 µM Clioquinol (CLQ), Picolinamide (PAM), Melatonin (MEL) or Resveratrol (RES) as single therapy for 24 hrs.

Figure 24:
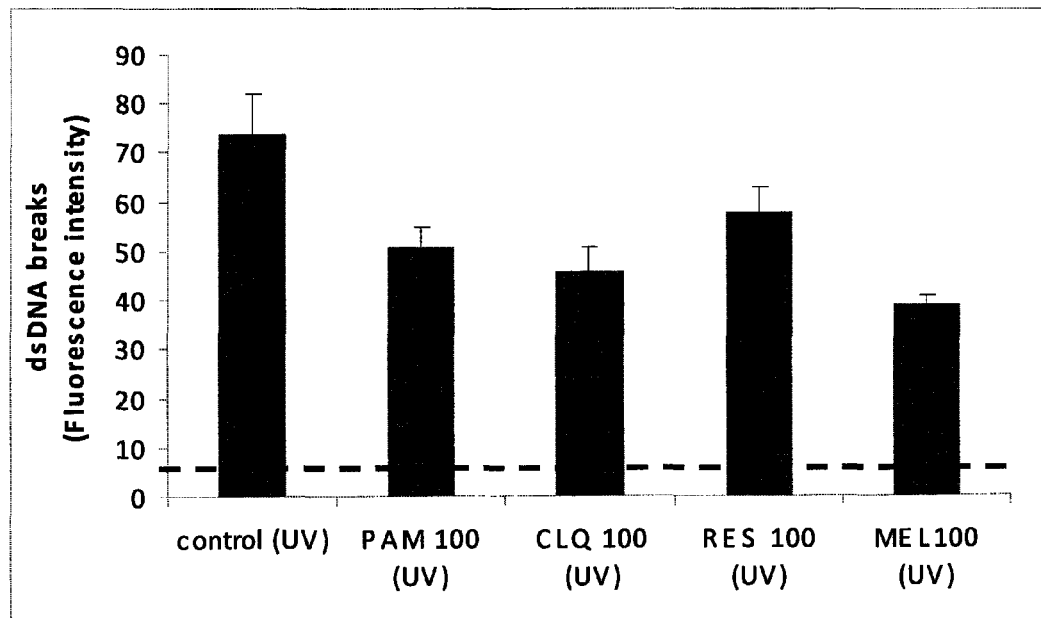
FIG. 24 is a graph showing the effect of mono therapy supplementation on DNA repair following treatment with RES (100 μM) or MEL (100 μM) or CLQ (0.1 μM) or PAM (100 μM) for 24 hr after UVB exposure, in human primary Fibroblasts.

Cells were left to incubate for 24 hrs before analysis of intracellular residual DNA damage (dsDNA breaks) (FIG. 24). When residual dsDNA breaks is less than that for the UV treatment control this indicates efficiency of DNA repair. FIG. 24 shows the effect of mono therapy supplementation on DNA repair following treatment with RES (100 µM), MEL (100 µM), CLQ (0.1 µM) or PAM (100 µM) for 24 hr after UVB exposure, in human primary Fibroblasts. The concentration used were equivalent to $EC_{100}$ for each therapeutic.

FIG. 24 shows that the amount of dsDNA breaks is significantly reduced following mono therapy with RES, PAM, CLQ or MEL. With the greatest apparent improvement observed for the MEL treated group with ~40% reduction in damaged DNA.

Figure 25:
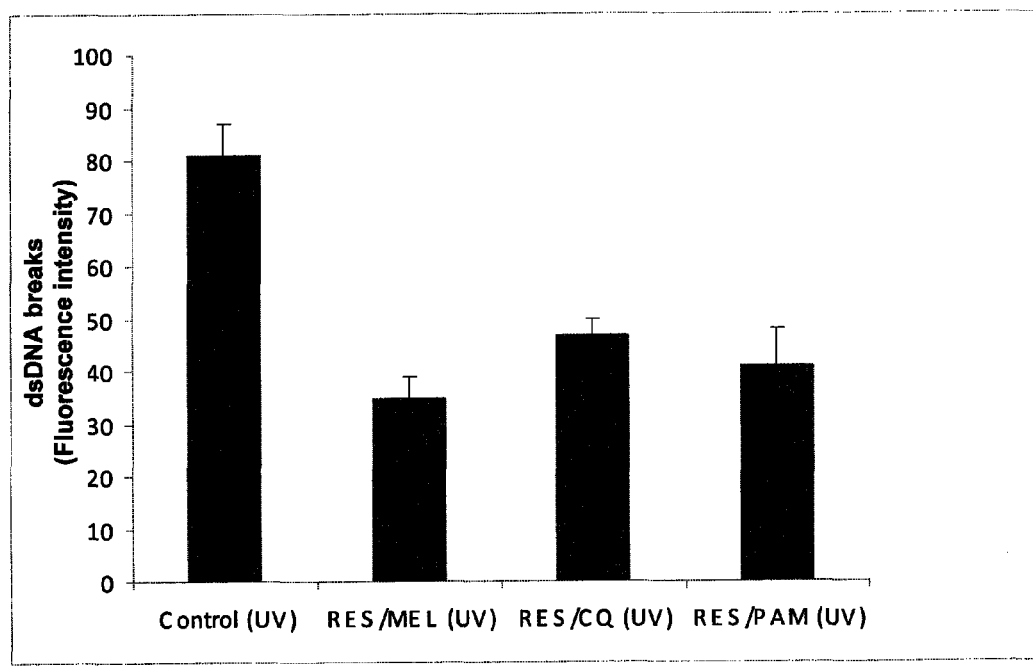
FIG. 25 is a graph showing the effect of dual therapy supplementation on DNA repair following treatment with RES+MEL, RES+CLQ, RES+PAM for 24 hr after UVB exposure, in human primary Fibroblasts. Concentrations used were equivalent to $EC_{50}/EC_{50}$, $EC_{10}/EC_{90}$, $EC_{90}/EC_{10}$ respectively.

FIG. 25 shows that the amount of dsDNA breaks is also significantly reduced following dual therapy with RES+MEL, RES+CLQ, RES+PAM. With the greatest improvement observed for the MEL treated group with >60% reduction in damaged DNA. FIG. 25 shows the effect of dual therapy supplementation on DNA repair following treatment with RES+MEL, RES+CLQ, RES+PAM for 24 hr after UVB exposure, in human primary Fibroblasts. Concentrations used were equivalent to $EC_{50}/EC_{50}$, $EC_{10}/EC_{90}$, $EC_{90}/EC_{10}$ respectively.

Figure 26:
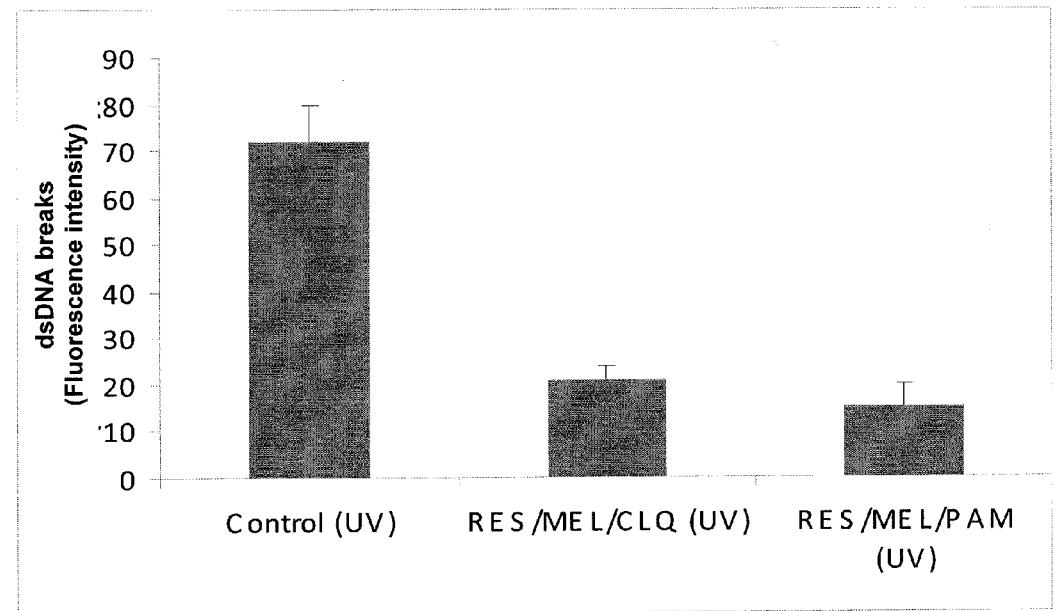
FIG. 26 is a graph showing the effect of triple therapy supplementation on DNA repair following treatment with RES+MEL+CLQ or RES+MEL+PAM for 24 hr after UVB exposure, in human primary Fibroblasts.

However, FIG. 26 shows that the amount of dsDNA breaks is even more significantly reduced following triple therapy with RES+MEL+CLQ or RES+MEL+PAM. The greatest improvement in DNA repair was observed for the RES+MEL+PAM treated group with >80% reduction in damaged DNA. FIG. 26 shows the effect of triple therapy supplementation on DNA repair following treatment with RES+MEL+CLQ or RES+MEL+PAM for 24 hr after UVB exposure, in human primary Fibroblasts.

Taken together, this data clearly shows that, dual therapies containing RES are much more successful in enhancing DNA repair (as was previously observed for regenerating intracellular NAD) compared any mono therapy (even at $EC_{100}$ concentrations). It also shows that triple therapies were even more effective than dual therapies (even using $EC_{100}$ equivalent combinations) at enhancing DNA repair.

Example 15

Effect of U.V. Radiation+/−Supplementation on DNA Repair in Cultures of Human Skin Cells (Keratinocytes)

Human skin cells (Keratinocytes) were grown at a density of $5 \times 10^6$ in PERMANOX® chamber-slides (NUNC) for 2 weeks. This method is commonly used in the industry and is well known to those skilled in the art. Accordingly, there is no need to detail the method utilised in this specification.

Cells were either left unexposed or exposed to 15 min UVB (~200 mJcm$^{-2}$). The culture medium was then supplemented with either 100 µM Clioquinol (CLQ), Picolinamide (PAM), Melatonin (MEL) or Resveratrol (RES) as single therapy for 24 hrs.

Figure 27:
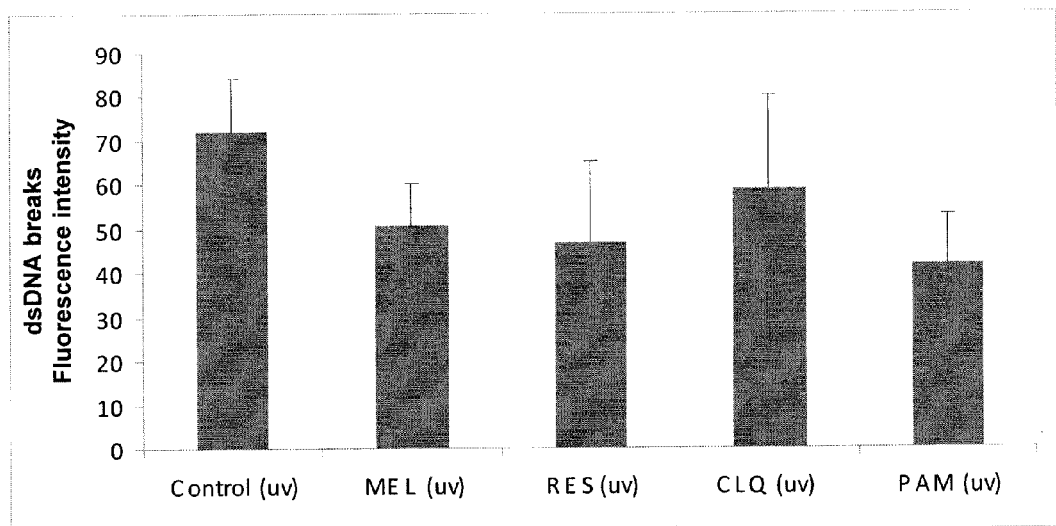
FIG. 27 is a graph showing the effect of mono therapy supplementation on DNA repair following treatment with RES (100 μM) or MEL (100 μM) or CLQ (0.1 μM) or PAM (100 μM) for 24 hr after UVB exposure, in human primary Keratinocytes.

Cells were left to incubate for 24 hrs before analysis of intracellular residual DNA damage (dsDNA breaks) (FIG. 27). When residual dsDNA breaks is less than that for the UV treatment control this indicates efficiency of DNA repair.

FIG. 27 shows that the amount of dsDNA breaks is significantly reduced following mono therapy with RES, PAM, CLQ or MEL. With the greatest apparent improvement observed for the MEL treated group with ~30% reduction in damaged DNA. FIG. 27 shows the effect of mono therapy supplementation on DNA repair following treatment with RES (100 µM), MEL (100 µM), CLQ (0.1 µM) or PAM (100 µM) for 24 hr after UVB exposure, in human primary Keratinocytes. The concentrations used were equivalent to $EC_{100}$ for each therapeutic.

Figure 28:
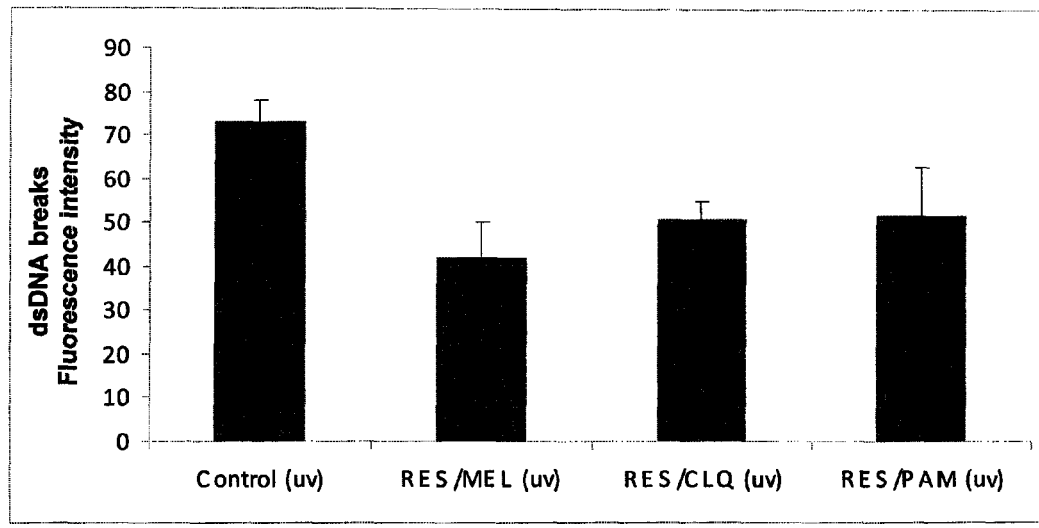
FIG. 28 is a graph showing the effect of dual therapy supplementation on DNA repair following treatment with RES+MEL, RES+CLQ, RES+PAM for 24 hr after UVB exposure, in human primary Keratinocytes. Concentrations used were equivalent to $EC_{50}/EC_{50}$, $EC_{10}/EC_{90}$, $EC_{90}/EC_{10}$ respectively.

FIG. 28 shows that the amount of dsDNA breaks is also significantly reduced following dual therapy with RES+MEL, RES+CLQ, RES+PAM. With the greatest improvement observed for the MEL treated group with ~40% reduction in damaged DNA. FIG. 28 shows the effect of dual therapy supplementation on DNA repair following treatment with RES+MEL, RES+CLQ, RES+PAM for 24 hr after UVB exposure, in human primary Keratinocytes. Concentrations used were equivalent to $EC_{50}/EC_{50}$, $EC_{10}/EC_{90}$, $EC_{90}/EC_{10}$ respectively.

Figure 29:
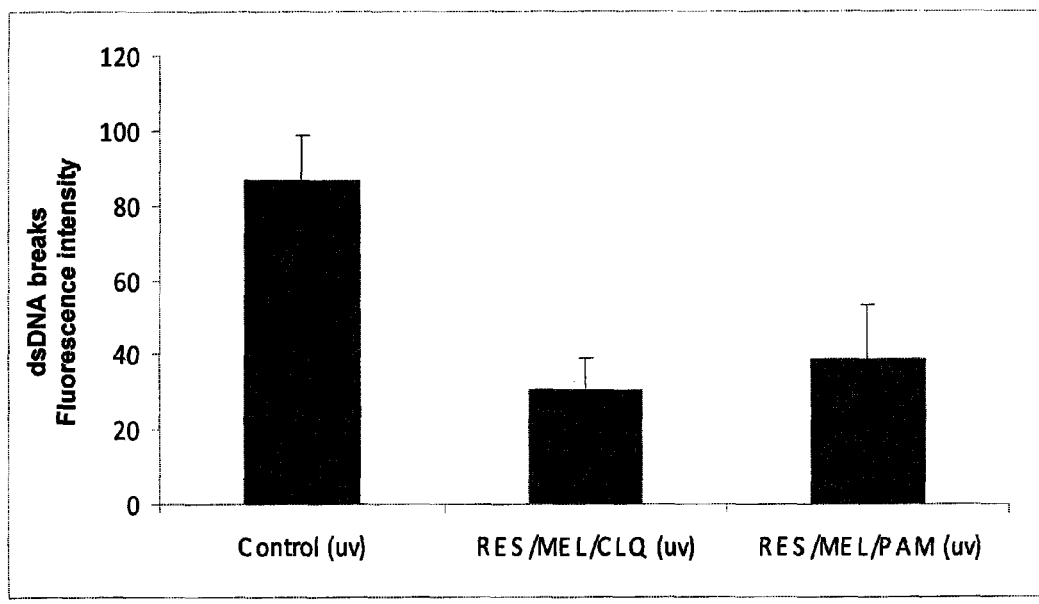
FIG. 29 is a graph showing the effect of triple therapy supplementation on DNA repair following treatment with RES+MEL+CLQ or RES+MEL+PAM for 24 hr after UVB exposure, in human primary Keratinocytes.

However, FIG. 29 shows that the amount of dsDNA breaks is even more significantly reduced following triple therapy with RES+MEL+CLQ or RES+MEL+PAM. The greatest improvement in DNA repair was observed for the RES+MEL+PAM treated group with ~60% reduction in damaged DNA. FIG. 29 shows the effect of triple therapy supplementation on DNA repair following treatment with RES+MEL+CLQ or RES+MEL+PAM for 24 hr after UVB exposure, in human primary Keratinocytes.

Taken together, this data clearly shows that, dual therapies are much more successful in enhancing DNA repair (as was previously observed for regenerating intracellular NAD) compared to any mono therapy (even at $EC_{100}$ concentrations). It also shows that triple therapies are even more effective than dual therapies (even using $EC_{100}$ equivalent combinations) at enhancing DNA repair.

Example 16

Synergistic Compositions

Human primary human foetal astrocytes were cultured as described in Guillemin et al. *J. Neurochem.* (2001) 78(4): 842-853. Intracellular NAD$^+$ levels were measured using the method described by Grant and Kapoor *J. Neurochem.* (1998) 70(4): 1759-1763. Intracellular NAD$^+$ concentration was adjusted for variations in cell number between cultures by measuring the amount of protein in the cell homogenate using the Bradford protein assay is derived by Bradford *Anal. Biochem.* (1976) 53: 452-458.

Approximately $1 \times 10^5$ cells were seeded into 24 well culture plates and maintained in culture for 24 hours as previously described in Guillemin et al. *J. Neurochem.* (2001) 78(4): pp. 842-853. Selected concentrations of individual drug or drug combinations (Clioquinol 10 µM, Melatonin 5

μM, resveratrol 100 μM) were added in 10 μL aliquots to 1 mL of medium. After 24 hours culture medium was removed and washed twice with replaced with phosphate buffered saline (PBS). 300 μL of PBS containing 100 μM $H_2O_2$ was then added to each culture well and left to incubate at 37° C. in 5% $CO_2$ for 15 minutes. The PBS was then aspirated from each culture and replaced with fresh homogenate mixture. Cells were then sonicated and the homogenate analysed for NAD+ (H) and total protein.

Figure 30:
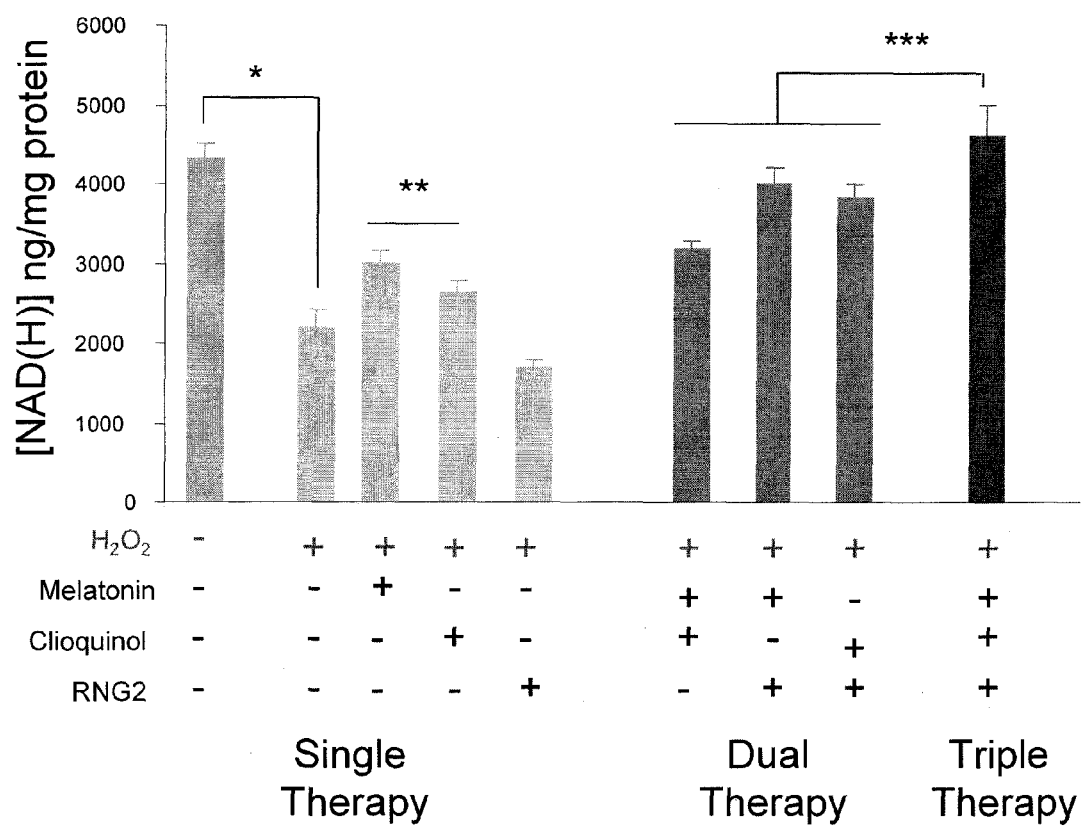
FIG. 30 is a graph showing the effect of 24 hr pre-treatment with an antioxidant (melatonin) and/or clioquinol), a chelator and/or resveratrol on intracellular NAD levels in human foetal astrocytes following 15 min of $H_2O_2$-induced oxidative stress. *p<0.05, p<0.05 compared to $H_2O_2$ alone, *p<0.05 compared to each dual therapy treatment.

FIG. 30 shows the effect of 24 hour pre-treatment with Melatonin—5 μM (antioxidant) and/or Clioquinol—10 μM ($Fe^{2+}/Cu^+$ Chelator) and/or resveratrol—100 μM (NMNAT enzyme activator) on intracellular $NAD^+$ levels following 15 min of $H_2O_2$ (100 μM) induced oxidative stress. $NAD^+$ levels were significantly higher in cells treated with triple therapy compared to treatment with any single agent or combination of any two agents.

$H_2O_2$ Treatment

FIG. 30 shows that cells treated with $H_2O_2$ results in a significant decrease in intracellular NAD levels. This result is due to hydroxyl radical (Fenton chemistry) induced DNA damage and resultant overactivation of the DNA repair enzyme PARP which uses NAD as a substrate.

Mono Drug Therapy

Pre-treatment with the potent antioxidant melatonin or the $Fe^{++}/Cu^+$ chelator clioquinol significantly reduced $NAD^+$ depletion (FIG. 30). However pre-treatment with resveratrol alone did not show a significant change in intracellular $NAD^+$ compared to oxidative ($H_2O_2$) insult alone.

Dual Drug Therapy

Pre-treatment with any two of, clioquinol, melatonin or resveratrol preserved $NAD^+$ levels following oxidative ($H_2O_2$) insult to a significantly greater degree that any mono drug therapy (FIG. 19). Dual therapy containing resveratol preserved $NAD^+$ levels to a significantly greater degree that therapies that did not contain resveratrol (FIG. 19), providing indication of a synergistic effect.

Triple Drug Therapy

Pre-treatment with all three of, clioquinol plus melatonin plus resveratrol preserved $NAD^+$ levels following oxidative ($H_2O_2$) insult to a significantly greater degree that any single or dual combination drug therapy (FIG. 19) (*$p<0.05$, $p<0.05$ compared to H2O2 alone, *$p<0.05$ compared to each dual therapy treatment).

INDUSTRIAL APPLICABILITY

The present invention can be utilised in respect of methods and compositions for inducing DNA repair and $NAD^+$ synthesis in a subject. Particularly, the invention can be utilised with respect to methods and pharmaceutical compositions for the prevention and treatment of conditions and diseases associated with oxidative stress and/or DNA damage.

The invention claimed is:

1. A method of treating a disease or condition associated with oxidative stress or DNA damage in a subject, wherein the disease or condition is characterized by the presence of excess oxidative compounds in the subject, the method consisting of:
   administering to the subject a composition consisting of a synergistic composition of:
      100 μM of resveratrol or a functionally equivalent analogue or derivative thereof effective to promote NAD+ synthesis in the subject;
      10 μM of clioquinol to reduce production of additional oxidative compounds in the subject; and
      5 μM of melatonin to minimize the oxidative activity in the subject.

2. The method according to claim 1, wherein the disease or condition includes a neurodegenerative disorder, accelerated aging of the skin, and/or DNA damage.

3. The method according to claim 1, wherein the neurodegenerative disorder is Alzheimer's disease or Parkinson's disease.

4. The method according to claim 2, wherein the DNA damage includes UV-induced DNA damage in the subject's skin cells.

5. The method according to claim 4, wherein the skin cells are keratinocytes and fibroblasts.

6. The method according to claim 2, wherein the disease or condition is cancer.

7. The method according to claim 2, wherein the disease or condition results from exposure to ultra-violet light, ionizing radiation, exposure to chemical agents, infection, inflammation, reduced mitochondrial efficiency, or a combination thereof.

8. The method according to claim 1, wherein the resveratrol or functionally equivalent analogue or derivative is a functionally equivalent analogue selected from the group consisting of hydroxylated resveratrol analogues, methoxylated resveratrol analogues, cis-resveratrol glucoside (cis-piceid), and trans-resveratrol-3-O-β-glucoside (trans-piceid).

9. The method according to claim 1, wherein the resveratrol or a functionally equivalent analogue or derivative thereof promotes NAD+ synthesis by upregulating nicotinamide mononucleotide adenylyl transferase (NMNAT) activity in the subject, thereby increasing the metabolism of nicotinamide (NAM).

10. The method according to claim 9, wherein the increase in the metabolism $NAD^+$ increases PARP enzyme activity, thereby further promoting DNA repair in the subject, and also providing a correlated increase in mammalian sirtuin enzyme activity, thereby promoting cell viability and longevity in the subject.

11. The method according to claim 10, wherein the PARP enzymes are selected from PARP-1 or PARP-2.

12. The method according to claim 10, wherein the mammalian sirtuin enzyme family members are selected from the group consisting of SIRT1, SIRT2, SIRT3, SIRT4, SIRT5, SIRT6, and SIRT7.

* * * * *